Figure 1:

(12) United States Patent
de Vries et al.

(10) Patent No.: US 7,465,459 B2
(45) Date of Patent: Dec. 16, 2008

(54) PIROPLASMID VACCINE

(75) Inventors: Erik de Vries, Rhenen (NL); Fasila Razzia Gaffar, Amsterdam (NL); Ana Patricia Yatsuda, Utrecht (NL); Theodorus Cornelis Schaap, Beugen (NL)

(73) Assignee: Universiteit Utrecht Holding B.V., Utrecht (NL)

( * ) Notice: Subject to any disclaimer, the term of this patent is extended or adjusted under 35 U.S.C. 154(b) by 0 days.

(21) Appl. No.: 10/571,667

(22) PCT Filed: Sep. 14, 2004

(86) PCT No.: PCT/EP2004/052169

§ 371 (c)(1),
(2), (4) Date: May 11, 2007

(87) PCT Pub. No.: WO2005/026199

PCT Pub. Date: Mar. 24, 2005

(65) Prior Publication Data

US 2007/0253974 A1 Nov. 1, 2007

(30) Foreign Application Priority Data

Sep. 14, 2003 (EP) .................. 03020898

(51) Int. Cl.
| | |
|---|---|
| A61K 39/00 | (2006.01) |
| A61K 39/018 | (2006.01) |
| A61K 38/00 | (2006.01) |
| C12N 1/20 | (2006.01) |
| C12N 1/00 | (2006.01) |
| C12N 15/00 | (2006.01) |
| C12N 5/00 | (2006.01) |
| C07K 1/00 | (2006.01) |
| C07H 21/02 | (2006.01) |

(52) U.S. Cl. .............. 424/270.1; 424/269.1; 435/252.3; 435/254.2; 435/320.1; 435/325; 530/300; 530/350; 536/23.1

(58) Field of Classification Search ........................ None
See application file for complete search history.

(56) References Cited

FOREIGN PATENT DOCUMENTS

WO    WO 90/11776    10/1990

OTHER PUBLICATIONS

Ellis, R.W. (Chapter 29 of "Vaccines" [Plotkin, S.A. et al. (eds) published by W. B. Saunders company (Philadelphia) in 1988.*
De Vos et al. Ann N Y Acad Sci 2000; 916:540-5.*
WC Brown et al. Parasitol Today. Jul. 1999;15(7):275-81.*
MC Jenkins, Veterinary Parasitology 101 (2001): 291-310.*
Abbas et al. Cellular and Molecular Immunology 4$^{th}$ ed. 2000 p. 360-362.*
De Vries, E. et al., "Analysis of Proteins involved in Erythrocyte Invasion by *Babesia bovis*", poster presented at Woodshole Conference, Aug. 2003.
Court, R.A., et al., "Mapping the T cell epitopes of the *Babesia bovis* antigen 12D3: implications for vaccine design" Parasite Immunology, 1998 20(1) 1-8, Blackwell Sci. Ltd.
Norimine, J., et al., "Imm

A

B

A          B

PIROPLASMID VACCINE

REFERENCE TO SEQUENCE LISTING

The material saved as "text document" under the file name "Substitute Sequence Listing" created on Feb. 28, 2006 is hereby incorporated by reference.

The invention relates to a Piroplasmid protein or an immunogenic fragment of said protein, to a nucleic acid encoding said Piroplasmid protein or said immunogenic fragment, to cDNA fragments recombinant DNA molecules and live recombinant carriers comprising said nucleic acid, to host cells comprising said cDNA fragments, recombinant DNA molecules and live recombinant carriers, to vaccines comprising a Piroplasmid protein or an immunogenic fragment of said protein, to methods for the preparation of such vaccines, to the use of such proteins or fragments, and to diagnostic tests.

Babesiosis is a disease, which has a geographically focal occurrence. The reason for this is that the pathogen is transmitted by ticks that feed on a certain reservoir of parasites present in a vertebrate population. Only where ticks are present, Babesiosis can occur. On balance, particularly in indigenous animals, the parasite coexists with the host without causing significant disease. In many cases Babesiosis becomes a problem because of man's activities through inbreeding of genetic traits and/or transporting animals to unfamiliar environments where Babesiosis is endemic (Callow, L. L. and Dalgliesh, R. J., 1982, in: "Immunology of Parasitic Infections", Cohen, S. and Warren, K. S. eds., p. 475-526, Blackwell Scientific).

Babesiosis also holds a threat as zoonotic agent for humans, not only to immunocompromised humans (Gray et al., 2002, Int. J. Med. Microbiol., vol. 291, p. 108-11).

Signs of disease in naturally acquired Babesiosis usually begin 7-21 days after infection. These symptoms include: fever, anorexia, depression, anaemia, haemoglobinuria and rapidly developing weakness. Increased lacrimation, salivation and muscle tremor commonly occur. Nervous signs may develop in terminal infections, and death may occur when the disease is left untreated. Coagulation disturbances lead to increased erythrocyte-stickiness. As a result the blood passage through the microvasculature is hampered, resulting in congestion of internal organs and decreased packed cell volumes (PCV). Also rupture of infected erythrocytes causes loss of large numbers of erythrocytes. These effects impair the oxygen supply to several tissues and subsequently lead to tissue damage as a result of anoxia.

Species from the Babesiidae have now been detected to infect most mammalian species of veterinary importance (Kuttler, K. L., in M. Ristic ed.: "Babesiosis of domestic animals and man". CRC Press, Inc., Boca Raton, Fla., 1988): Cow (*B. divergens, B. bovis, B. bigemina*), Swine (*B. trautmanni, B. perroncitoi*), Sheep (*B. ovis, B. motasi*), Horse (*B. equi, B. cabali*), Dog (*B. canis, B. rossi, B. vogel*), and Cat (*B. felis, B. cati*). In all these species death or more or less severe economical losses (reduction in quality or quantity of meat, milk, wool, or offspring), or severe reduction in well-being are caused either as a result of the Babesia infection directly, or through facilitation of secondary infections.

Closely related to *Babesia* are *Theileria* parasites. These also belong to the taxonomic group of the Piroplasmida, and show many biological and epidemiological relationships to *Babesia*. Well known *Theileria* species of veterinary importance are *T. parva, T. annulata*, and *T. sergenti*.

Medications exist to cure an established Babesia or Theileria infection, for instance dogs, horses and cows can be treated with imidocarb dipropionate. However such an injection is painful due to tissue irritation. Further it suffers the drawbacks common to such anti-parasitics: the prevention of a build up of immunological memory, potential toxicity, and possible build up of resistance.

It has been shown that Babesiosis and Theileriosis can be controlled by vaccination with live vaccines (reviewed in: Jenkins, M. 2001, Vet Parasitol., vol. 101, p. 291-310). Such vaccines are produced by harvesting erythrocytes from infected animals. For some but not all *Babesia* species in vitro erythrocyte cultures have been developed, to increase the number of parasites. The infected erythrocytes from the animal or the cultures, also known as "stabilates", are then used to vaccinate animals.

Stabilates for *Theileria* are produced in a similar fashion. In fact, because the need for an effective vaccine is so high, *Theileria* stabilates have even been produced from the salivary glands of infected ticks.

General disadvantages of such live parasitic vaccines are that the inoculation material is largely uncontrolled, highly variable in its composition, biologically unsafe, and on the whole the process is unethical through the use of a large number of experimental animals. Additionally, Piroplasmid parasites are very unstable; they must be kept away from free oxygen or will die quickly.

Alternatively, not the parasite-infected erythrocytes themselves are used for vaccination, but the serum from the infected host, or the supernatant of an in vitro culture. Such surrounding liquids of infected erythrocytes contain so-called Soluble Parasite Antigens (SPA). Little is known about the composition of these preparations. It has been suggested that the protective activity is due to the immunising capacity of antigens of the merozoite surface coat in the serum or medium, a structure that is left behind during the process of invasion of the erythrocyte (Ristic, M. and Montenegro-James, S., 1988, in: "Babesiosis of Domestic Animals and Man", Ristic, M. ed., p. 163-190, CRC Press). In addition, during in vitro culture a number of parasites die, thereby (internal) parasitic antigens are released into the culture medium.

Such SPA preparations are capable of inducing an immune response that, although not necessarily affecting the parasite, sufficiently reduces the clinical manifestations of infection (Schetters and Montenegro-James, S., 1995, Parasitology Today, vol. 11, p. 456-462). For instance SPA from culture supernatant of an in vitro culture of *Babesia canis* parasite infected erythrocytes (Pirodog®) induces immunity against homologous (but not to heterologous) challenge infection.

In general, SPA based vaccines bear the same disadvantages as the live parasitic vaccines do, in that they are largely uncharacterised, highly variable and require many precautions to be biologically safe. Additionally the production of such vaccines is very difficult to scale up, as that requires the infection, housing and harvesting from samples of experimental animals to provide parasites, erythrocytes, and/or serum.

It is an object of the invention to provide proteins and fragments thereof that can serve in effective vaccines for prevention or amelioration of infection with a Piroplasmid organism, that are well defined, safe, stable, and with a production that is easy to scale up.

It was surprisingly found now that a vaccine comprising one or more of five novel Piroplasmid proteins, or an immunogenic fragment of one or more of said proteins incorporates all these advantageous characteristics.

Many disadvantages of live parasite- and SPA vaccines can now be overcome by the use of such a Piroplasmid protein or of an immunogenic fragment of said protein in vaccines. Such a protein is highly defined, biologically safe, the product can be stabilized much better than whole live parasites, and its production can be easily scaled up It was surprisingly found that antibodies raised against Piroplasmid proteins or immunogenic fragments of said proteins, effectively inhibited the invasion of parasites into host cells, and thereby interfered with the parasites' infection cycle. The proteins are therefore called: invasion inhibiting antigen (IIA).

The process of the invasion by a Piroplasmid parasite of its host cell is one of the critical steps in the establishment of parasitic infection. By interfering at this level through induction of antibodies that interfere with this step, the initial entry of parasites into the cells of the host is inhibited. This prevents, or at least diminishes, the level of infection or the clinical signs of disease in a host, and consequently the severity of disease. Also the further spread of the disease in the environment is halted or diminished because less ticks will become carriers when feeding on vaccinated hosts, ergo the infection pressure in the environment is decreased.

Piroplasmid IIA's, which can induce protective immune responses that lead to antibodies that inhibit Piroplasmid parasite invasion, can be detected in Piroplasmid parasites, in cultures of proliferating parasites, and in infected cells by specific antisera. These specific antisera recognize these IIA also in 1-D and 2-D (2 dimensional) Western blots of lysates of infected cells, of parasites or their cultures.

The Piroplasmid IIA's can be expressed in an expression system. Proteins, or their fragments, expressed in this way can be used to formulate a vaccine which protects mammalians from disease or its clinical signs upon infection by a Piroplasmid organism, through the induction of specific antibodies or antigen-specific lymphocytes.

Therefore the invention provides a Piroplasmid protein characterised in that said protein comprises an amino acid sequence having a similarity of at least 70%, preferably 75%, more preferably 80, 85, 90, 92, 94, 95, 96, 97, 98, 99, or 100% similarity in that order of preference, with the amino acid sequence depicted in SEQ ID NO: 2 or 4, or an immunogenic fragment of said protein.

The invention also provides a Piroplasmid protein characterised in that said protein comprises an amino acid sequence having a similarity of at least 70%, preferably 75%, more preferably 80, 85, 90, 92, 94, 95, 96, 97, 98, 99, or 100% similarity in that order of preference, with the amino acid sequence depicted in SEQ ID NO: 6 or 8, or an immunogenic fragment of said protein.

The invention additionally provides a Piroplasmid protein characterised in that said protein comprises an amino acid sequence having a similarity of at least 70%, preferably 75%, more preferably 80, 85, 90, 92, 94, 95, 96, 97, 98, 99, or 100% similarity in that order of preference, with the amino acid sequence depicted in SEQ ID NO: 10, or an immunogenic fragment of said protein.

Typical examples of the Piroplasmid proteins of the invention are:

Piroplasmid IIA number 1 from *Babesia bovis* (BIIA1) the amino acid sequence of which is presented in SEQ ID NO: 2;

Piroplasmid IIA number 1 from *Theileria annulata* (TIIA1) the amino acid sequence of which is presented in SEQ ID NO: 4;

Piroplasmid IIA number 2 from *B. bovis* (BIIA2) the amino acid sequence of which is presented in SEQ ID NO: 6;

Piroplasmid IIA number 2 from *T. annulata* (TIIA2) the amino acid sequence of which is presented in SEQ ID NO: 8;

Piroplasmid IIA number 3 from *B. bovis* (BIIA3) the amino acid sequence of which is presented in SEQ ID NO: 10.

The term "protein" is meant to incorporate a molecular chain of amino acids. A protein is not of a specific length, structure or shape and can, if required, be modified in vivo or in vitro, by, e.g. glycosylation, amidation, carboxylation, phosphorylation, or changes in spatial folding. Inter alia, peptides, oligopeptides and polypeptides are included within the definition of protein. A protein can be of biologic and/or of synthetic origin.

A "Piroplasmid protein" according to the invention is a protein, which is obtainable from an organism of the Piroplasmids.

Preferably the Piroplasmid protein is obtainable from an organism selected from the group consisting of the species *Babesia divergens, B. bovis, B. motasi, B. caballi, B. equi, B. canis, B. rossi, B. vogeli, B. felis, B. cati, B. ovis, B. trautmanni, B. bigemina, B. microti, B. gibsoni, Theileria annulata, T. parva, T. equi, T. felis, T. canis* and *T. sergenti.*

More preferably the Piroplasmid protein is obtainable from an organism selected from the group consisting of the species *Babesia bovis, B. caballi, B. equi, B. canis, B. rossi, B. bigemina, Theileria annulata, T. parva* and *T. equi.*

Even more preferably, the Piroplasmid protein is obtainable from an organism selected from the group consisting of the species *Babesia bovis* and *Theileria annulata.*

Most preferably the Piroplasmid protein is obtainable from *Babesia bovis.*

With respect to the current taxonomic classification, the skilled person will realise this may change over time as new insights lead to reclassification into new or other taxonomic groups. However, as this does not change the protein repertoire of the organism involved, only its classification, such re-classified organisms are considered to be within the scope of the invention. This is especially relevant for such closely related families as Babesiidae and Theileriidae. For example: *Babesia equi* was recently re-classified as *Theileria equi.*

In order to be antigenic, a fragment of a protein needs to be of a certain length; too small fragments will not be processed by antigen presenting cells to fragments that are able as such to associate with MHC molecules, which association is required for proper antigen presentation to lymphocytes. For MHC I receptor binding an antigen fragment that encompasses the epitope consists of at least 8-11 amino acids, and for MHC II receptor binding at least 11-15 amino acids (reviewed e.g. by R. N. Germain & D. H. Margulies, 1993, Annu. Rev. Immunol., vol. 11, p. 403-450, in: "The biochemistry and cell biology of antigen processing and presentation"). Protein fragments shorter than this may not be antigenic as such: they need to be coupled to a carrier, such as KLH, BSA or the like, using techniques known in the art. When coupled such short fragments may well be able to induce an immune response that is within the scope of the invention.

For the invention, an "epitope" is that part of an antigenic molecule that reacts with the antigen receptor of a T- and/or B-lymphocyte. An epitope according to the invention will therefore induce and/or activate specific T- and/or B-cells such that these cells give rise to an immune reaction that interferes with the course of an infection or disease. Thus, through such epitopes, a protein can induce antibodies and/or generate an immune response.

An "immunogenic fragment" is understood to be an epitope-containing antigenic fragment of a Piroplasmid protein that has the capability to induce immune responses directed against such Piroplasmid proteins, with the provision that such antibodies are capable of interfering with the process of invasion. It will be explained below how such immunogenic fragments can be found.

An immunogenic fragment of a Piroplasmid protein according to the invention comprises at least 10 amino acids taken from the amino acid sequence of a Piroplasmid protein according to the invention.

Preferably such a fragment comprises 12, 15, 20, 30, 40, 50, 75, 100, 150, 200, or 300 amino acids, in that order of preference, taken from the amino acid sequence of a Piroplasmid protein according to the invention.

For instance an immunogenic fragment of a Piroplasmid protein according to the Invention is formed by a part of the protein that lacks the N-terminal signal sequence and/or the C-terminal sequence. Other fragments are for instance those comprising a specific epitope from a Piroplasmid IIA protein. Such epitopes may be determined by the methods outlined below. All such immunogenic fragments are within the scope of the invention.

Identification of immunogenic fragments and/or epitopes of a Piroplasmid protein according to the invention, can be easily performed by a variety of straightforward techniques, for instance by the so-called PEPSCAN method, or via computer algorithms that make comparisons to known fragments and/or epitopes.

The PEPSCAN method (WO 84/03564, and WO 86/06487, and H. Geysen et al., Proc. Natl. Acad. Sci. USA 1984, vol. 81, p. 3998-4002, and J. of Immunol. meth. 1987, vol. 102, p. 259-274), is an easy to perform, quick and well-established method for the detection of immunologic determinants of a protein. It comprises the synthesis of a series of peptide fragments progressively overlapping the protein under study, and subsequent testing of these polypeptides with specific antibodies to the protein to identify which of these are able to bind to the antigen receptor of T- and/or B-lymphocytes. Such antibodies to the proteins according to the invention can be obtained by making polyclonal or monoclonal antibodies, by using techniques well known in the art.

The use of computer algorithms in the designation of specific protein fragments as the immunologically important epitopes on the basis of their sequential and/or structural agreement with epitopes that are known, is also a well-known technique. The determination of these regions can be based on a combination of the hydrophilicity criteria according to Hopp and Woods (Proc. Natl. Acad. Sci. USA 1981, vol. 78, p. 3824-3828), and the secondary structure aspects according to Chou and Fasman (Advances in Enzymology 1987, vol. 47, p. 45-148, and U.S. Pat. No. 4,554,101). Immunogenic epitopes can likewise be predicted from the protein's amino acid sequence by computer with the aid of Berzofsky's amphiphilicity criterion (, Science 1987, vol. 235, p. 1059-1062 and U.S. patent application NTIS U.S. Ser. No. 07/005, 885). A condensed overview of the use of these methods is found in Shan Lu (common principles: Tibtech 1991, vol. 9, p. 238-242), Lu (review: Vaccine 1992, vol. 10, p. 3-7), and Berzofsky (HIV-epitopes; 1991, The FASEB Journal, vol. 5, p. 2412-2418).

An illustration of the effectiveness of using these methods was published by H. Margalit et al. (J. of Immunol. 1987, vol. 138, p. 2213-2229) who describe success rates of 75% in the prediction of T-cell epitopes using such methods. Still further proof is the successful prediction of the 6 antigenic peptides from BIIA1 and BIIA2, as outlined in Example 1, section 1.1.5.

Subsequently, it has to be determined if an epitope found using the methods described above is indeed capable of interfering with the process of invasion. This can however be done very quickly and easily in a simple in vitro invasion inhibition experiment. Such an experiment is described in Example 1.1.11.

The percentage of similarity of an amino acid sequence with a protein according to the invention must be determined by amino acid alignment to the full-length amino acid sequence of SEQ ID NO: 2, 4, 6, 8, or 10.

The percentage of similarity with a protein according to the invention must be determined with the computer program "BLAST 2 SEQUENCES" by selecting sub-program: "BlastP" (T. Tatusova & T. Madden, 1999, FEMS Microbiol. Letters, vol. 174, p. 247-250), that can be found at www.ncbi.nim.nih.gov/blast/bl2seq/bl2.html. The comparison-matrix that is used is: "Blosum62", with the default parameters: open gap penalty: 11; extension gap penalty: 1; and gap x_dropoff: 50.

This program lists the percentage of amino acids that are identical as "Identities", and the percentage of amino acids that are similar as "Positives". "Similar" amino acids are those amino acids that are identical plus those that are equivalent; "equivalent" amino acids are described below.

It will be understood that, for a particular Piroplasmid protein, natural variations exist between the proteins associated with individual strains or species of Piroplasmids. These variations may be demonstrated by (an) amino acid difference(s) in the overall sequence or by deletions, substitutions, insertions, inversions or additions of (an) amino acid(s) in said sequence. Amino acid substitutions, which do not essentially alter biological and immunological activities, have been described, e.g. by Neurath et al. (1979, in: "The Proteins", Academic Press New York). Amino acid replacements between related amino acids or replacements which have occurred frequently in evolution are, i.a. Ser/Ala, Ser/Gly, Asp/Gly, Asp/Asn, Ile/Val (see Dayhof, M.D., 1978, "Atlas of protein sequence and structure", Nat. Biomed. Res. Found., Washington D.C. vol. 5, suppl. 3). Other common amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Such related and commonly substituted amino acids are termed "equivalent". Based on this information, Lipman and Pearson developed a method for rapid and sensitive protein comparison (Science 1985, vol. 227, p. 1435-1441) and determining the functional similarity between proteins. Such amino acid substitutions of the exemplary embodiments of this invention, as well as variations having deletions and/or insertions are within the scope of the invention as long as the resulting proteins retain the capability of inducing immune responses that inhibit Piroplasmid parasite proliferation, for instance antibodies that inhibit Piroplasmid parasite invasion. Such variations in the amino acid sequence of a certain Piroplasmid protein according to the invention are considered as "biological- or functional homologs", and are all within the scope of the invention.

This explains why a Piroplasmid protein according to the invention, when isolated from different Piroplasmid species, may have a similarity down to 70% with for example the amino acid sequences depicted in SEQ ID NO: 2, 4, 6, 8, or 10 while still representing the same protein with the same characteristics, in the example presented: to be able to induce antibodies that inhibit Piroplasmid parasite invasion.

When comparing Piroplasmid proteins according to the invention amongst themselves, Piroplasmid proteins according to the invention obtained from different Piroplasmid organisms typically have over 50% amino acid similarity;

when obtained from different *Babesia* species, such proteins typically have over 85% amino acid similarity, and when obtained from different isolates from *B. bovis*, such proteins typically have over 95% amino acid similarity.

The preferred way to produce the Piroplasmid proteins according to the invention is by using genetic engineering techniques and recombinant expression systems. These may comprise using nucleic acids, cDNA fragments, recombinant DNA molecules, live recombinant carriers, and/or host cells.

Therefore, another aspect of the invention relates to a nucleic acid, characterised in that said nucleic acid encodes a Piroplasmid protein according to the invention, or an immunogenic fragment of said protein.

In an embodiment the nucleic acid according to the invention comprises the nucleic acid sequence depicted in SEQ ID NO: 1, 3, 5, 7, or 9.

The term "nucleic acid" is meant to incorporate a molecular chain of desoxy- or ribonucleic acids. A nucleic acid is not of a specific length, therefore polynucleotides, genes, open reading frames (ORF's), probes, primers, linkers, spacers and adaptors, consisting of DNA and/or RNA, are included within the definition or nucleic acid. A nucleic acid can be of biologic and/or synthetic origin. The nucleic acid may be in single stranded or double stranded form. The single strand may be in sense or anti-sense orientation. Also included within the definition are modified RNAs or DNAs. Modifications in the bases of the nucleic acid may be made, and bases such as Inosine may be incorporated. Other modifications may involve, for example, modifications of the backbone.

The term "encodes" is meant to incorporate: providing the possibility of protein expression, i.a. through transcription and/or translation when brought into the right context.

A nucleic acid according to the invention encodes a Piroplasmid protein according to the invention, or encodes an immunogenic fragment of said protein.

A nucleic acid according to the invention has a minimal length of 30 nucleotides. Preferably a nucleic acid according to the invention comprises 40, 50, 100, 250, 500, 1000, or 1500 nucleotides in that order of preference.

A nucleic acid according to the invention for instance is a nucleic acid encoding a Piroplasmid protein according to the invention that lacks the N-terminal signal sequence and/or the C-terminal sequence. Other nucleic acids may comprise a sequence encoding a specific epitope of a Piroplasmid protein. Such nucleic acids are all within the scope of the invention.

Excluded from the nucleic acids according to the invention are the following sequences:

with regard to BIIA1 (SEQ ID NO: 1), the EST sequences:
B_bovis-11e05.plc
B_bovis-344e09.qlc
B_bovis-384f06.qlc
B_bovis-261d05.qlc
B_bovis-5e5.plc
B_bovis-373g01.qlc
B_bovis-418b06.qlc
B_bovis-375d02.qlc
B_bovis-407d03.qlc
B_bovis-284-f07.qlc
with regard to BIIA1 (SEQ ID NO: 1), the assembled contigs:
Bbovis.CONTIG.1029
Bbovis.CONTIG.227
With regard to BIIA2 (SEQ ID NO: 5) the EST sequences:
B_bovis-417g12.qlc
B_bovis-376a10.qlc with regard to TIIA2 (SEQ ID NO: 7), the assembled contig:
gnl|Sanger_5874|Contig1548
with regard to TIIA1 (SEQ ID NO: 3), the assembled contig:
gnl|Sanger_5874|Contig1

The EST and contig sequences regarding BIIA1 and BIIA2 are available through the Sanger Institute's sequencing genomics projects' Internet web page.

The contig sequences regarding TIIA1 and TIIA2 are available through the NCBI BLAST server by selecting Apicomplexa from the United States' National Institutes of Health's National Library of Medicine's National Center for Biotechnology Information Eukaryotic genomes' BLAST Internet page.

The percentage of identity between nucleic acids according to the invention is determined with the computer program "BLAST 2 SEQUENCES" by selecting sub-program: "BlastN" (T. Tatusova & T. Madden, 1999, FEMS Microbiol. Letters, vol. 174, p. 247-250), that can be found at www.ncbi.nlm.nih.gov/blast/bl2seq/bl2.html. Parameters that are used are the default parameters: reward for a match: +1; penalty for a mismatch: −2; open gap penalty: 5; extension gap penalty: 2; and gap x_dropoff: 50. Unlike the output of the BlastP program described above, the BlastN program does not list similarities, only identities: the percentage of nucleotides that are identical are indicated as "Identities".

It is well known in the art, that many different nucleic acids can encode one and the same protein. This is a result of what is known in molecular biology as "wobble", or the "degeneracy of the genetic code", wherein several codons or triplets of mRNA will cause the same amino acid to be attached to the chain of amino acids growing in the ribosome during translation. It is most prevalent in the second and especially the third base of each triplet encoding an amino acid. This phenomenon can result in a heterology of about 30% for two different nucleic acids that still encode the same protein. Therefore, two nucleic acids having a nucleotide sequence identity of about 70% can still encode one and the same protein.

Another approach for deciding if a certain nucleic acid sequence is or is not a nucleic acid sequence according to the invention, relates to the question if that certain nucleic acid sequence does hybridise under stringent conditions to any of the nucleotide sequences depicted in SEQ ID NO: 1, 3, 5, 7, and 9.

If a nucleic acid sequence hybridises under stringent conditions to the nucleotide sequence as depicted in SEQ ID NO: 1, 3, 5, 7, and 9, it is considered to be a nucleic acid sequence according to the invention.

The definition of stringent conditions follows from the formula for the melting temperature Tm of Meinkoth and Wahl (1984, Anal. Biochem., vol. 138, p. 267-284):

$$Tm=[81.5^\circ C.+16.6(\log M)+0.41(\% GC)-0.61(\% formamide)-500/L]-1^\circ C./1\% mismatch$$

In this formula, M is molarity of monovalent cations; % GC is the percentage of guanosine and cytosine nucleotides in the DNA; L is the length of the hybrid in base pairs; and mismatch is the lack of an identical match.

Stringent conditions are those conditions under which nucleic acid sequences or fragments thereof still hybridise, if they have a mismatch of 30% (i.e. if they are only 70% identical) to the nucleic acid sequence as depicted in any of the SEQ ID NO's: 1, 3, 5, 7, and 9.

Nucleic acids encoding the Piroplasmid proteins according to the invention can be obtained from member species of the Piroplasmida.

However in a more preferred embodiment, the nucleic acids encoding a Piroplasmid protein or immunogenic fragments of said protein according to the invention are characterised in that they are obtainable from an organism selected from the group consisting of the species *Babesia divergens, B. bovis, B. motasi, B. caballi, B. equi, B. canis, B. rossi, B. vogeli, B. felis, B. cati, B. ovis, B. trautmanni, B. bigemina, B. microti, B. gibsoni, Theileria annulata, T. parva, T. equi, T. felis, T. canis* and *T. sergenti.*

More preferably the nucleic acids are obtainable from an organism selected from the group consisting of the species *Babesia bovis, B. caballi, B. equi, B. canis, B. rossi, B. bigemina, Theileria annulata, T. parva* and *T. equi.*

The possibility of species being taxonomically re-classified or described as new species has been discussed above. As this does not change the organism's genome, such reclassified organisms are also within the scope of the invention.

Also within the scope of the invention are Piroplasmid proteins, immunogenic fragments of said proteins and nucleic acids encoding such Piroplasmid proteins or fragments thereof from non-mammalian Piroplasmids, due to the high conservation of the genes and proteins of the Piroplasmid proteins according to the invention. Such related proteins, or their genes may be called paralogs or orthologs.

Nucleic acids encoding a Piroplasmid protein according to the invention can be obtained, manipulated and expressed by standard molecular biology techniques that are well-known to the skilled artisan, and are explained in great detail in standard text-books like Sambrook & Russell: "Molecular cloning: a laboratory manual" (2001, Cold Spring Harbour Laboratory Press; ISBN: 0879695773). One such type of manipulations is the synthesis of a cDNA fragment from RNA, preferably from mRNA that can be isolated from parasites, or parasite-infected cells or -organisms by techniques known in the art.

Therefore, in another aspect, the invention relates to a cDNA fragment according to the invention.

The preferred method of obtaining a cDNA fragment by reverse transcription is through a polymerase chain reaction (PCR) technique. Standard techniques and protocols for performing PCR are for instance extensively described in C. Dieffenbach & G. Dveksler: "PCR primers: a laboratory manual" (1995, CSHL Press, ISBN 879694473).

In a preferred embodiment, the invention relates to a recombinant DNA molecule comprising a nucleic acid according to the invention, or a cDNA fragment according to the invention, said nucleic acid or said cDNA fragment being under the control of a functionally linked promoter.

To construct a recombinant DNA molecule according to the invention, preferably DNA plasmids are employed. Such plasmids are useful e.g. for enhancing the amount of DNA-insert, as a probe, and as tool for further manipulations. Examples of such plasmids for cloning are plasmids of the pBR, pUC, and pGEM series; all these are available from several commercial suppliers.

The nucleic acid encoding a Piroplasmid protein according to the invention or an Immunogenic fragment of said protein, can be cloned into separate plasmids and be modified to obtain the desired conformation using techniques well known in the art. However they may also be combined into one construct for improved cloning or expression purposes.

Modifications to the coding sequences encoding a Piroplasmid protein according to the invention or an immunogenic fragment thereof may be performed e.g. by using restriction enzyme digestion, by site directed mutations, or by polymerase chain reaction (PCR) techniques.

For the purpose of protein purification or -detection, or improvement of expression level, additional nucleic acids may be added. This may result in the final nucleic acid comprised in the cDNA fragment, or in the recombinant DNA molecule being larger than the sequences required for encoding a Piroplasmid protein. When such additional elements are inserted in frame, these become an integral part of the Piroplasmid protein that is expressed. Such fused proteins are also within the scope of the invention An essential requirement for the expression of a nucleic acid, cDNA fragment, or recombinant DNA molecule is that these are operably linked to a transcriptional regulatory sequence such that this is capable of controlling the transcription of the nucleic acid, cDNA, or recombinant DNA. Transcriptional regulatory sequences are well known in the art and comprise i.a. promoters and enhancers. It is obvious to those skilled in the art that the choice of a promoter extends to any eukaryotic, prokaryotic or viral promoter capable of directing gene transcription, provided that the promoter is functional in the expression system used.

In a more preferred embodiment, the invention relates to a live recombinant carrier comprising a nucleic acid according to the invention or a cDNA fragment according to the invention, said nucleic acid or said cDNA fragment being under the control of a functionally linked promoter, or a recombinant DNA molecule according to the invention.

Such live recombinant carriers (LRC's) are e.g. micro-organisms such as bacteria, parasites and viruses in which additional genetic information has been cloned, in this case a nucleic acid, a cDNA, or a recombinant DNA molecule, encoding a Piroplasmid protein according to the invention or an immunogenic fragment thereof. Target mammalians inoculated with such LRC's will produce an immunogenic response not only against the immunogens of the carrier, but also against the heterologous protein(s) or immunogenic fragment(s) for which the genetic code is additionally cloned into the LRC, e.g. a sequence encoding a Piroplasmid protein according to the invention, or an immunogenic fragment thereof.

As an example of bacterial LRC's, attenuated *Salmonella* strains known in the art can attractively be used.

Alternatively, live recombinant carrier parasites have i.a. been described by Vermeulen, A. N. (Int. Journ. Parasitol. 1998, vol. 28, p. 1121-1130).

LRC viruses may be used as a way of transporting a nucleic acid into a target cell. Live recombinant carrier viruses are also called vector viruses. Viruses often used as vectors are Vaccinia viruses (Panicali et al. 1982, Proc. Natl. Acad. Sci. USA, vol. 79, p. 4927), Herpesviruses (EP 0473210-A2), and Retroviruses (Valerio, D. et al. 1989, in: Baum, S. J., Dicke, K. A., Lotzova, E. and Pluznik, D. H. (Eds.), "Experimental Haematology today", Springer Verlag, New York: pp. 92-99).

The technique of in vivo homologous recombination, well known in the art, can be used to introduce a recombinant nucleic acid according to the invention into the genome of an LRC bacterium, parasite or virus of choice, capable of inducing expression of the inserted nucleic acid, cDNA or recombinant DNA according to the invention in the host animal.

Bacterial, yeast, fungal, insect, and vertebrate cell expression systems are used as host cells for expression purposes very frequently. Such expression systems are well known in the art and generally available, e.g. commercially through Invitrogen (the Netherlands).

Therefore, in an even more preferred embodiment, the invention relates to a host cell comprising a nucleic acid according to the invention, a cDNA fragment according to the invention, said nucleic acid or said cDNA fragment being under the control of a functionally linked promoter, a recombinant DNA molecule according to the invention, or a live recombinant carrier according to the invention.

A host cell to be used for expression of a Piroplasmid protein according to the invention may be a cell of bacterial origin, e.g. from *Escherichia coli, Bacillus subtilis, Lactobacillus* sp. or *Caulobacter crescentus*, in combination with the use of bacteria-derived plasmids or bacteriophages for expressing the sequence encoding a Piroplasmid protein. The host cell may also be of eukaryotic origin, e.g. yeast-cells in combination with yeast-specific vector molecules, or higher eukaryotic cells, like insect cells (Luckow et al., 1988, Biotechnology, vol. 6, p. 47-55) in combination with vectors or recombinant baculoviruses; plant cells in combination with e.g. T-plasmid based vectors or plant viral vectors (Barton, K. A. et al., 1983, Cell, vol. 32, p. 1033); or mammalian cells like Hela cells, Chinese Hamster Ovary cells or Crandell-Rees feline kidney-cells, also with appropriate vectors or recombinant viruses.

Next to these expression systems, plant cell, or parasite-based expression systems are attractive expression systems. Parasite expression systems are e.g. described in the French Patent Application, publication number 2 714 074, and in U.S. NTIS publication no. U.S. Ser. No. 08/043,109 (Hoffman, S. & Rogers, W., 1993). Plant cell expression systems for polypeptides for biological application are e.g. discussed in R. Fischer et al. (Eur. J. of Biochem. 1999, vol. 262, p. 810-816), and J. Larrick et al. (Biomol. Engin. 2001, vol. 18, p. 87-94).

Expression may also be performed in so-called cell-free expression systems. Such systems comprise all essential factors for expression of an appropriate recombinant nucleic acid, operably linked to a promoter that will function in that particular system. Examples are the *E. coli* lysate system (Roche, Basel, Switzerland), or the rabbit reticulocyte lysate system (Promega corp., Madison, USA).

The Piroplasmid protein according to the invention or immunogenic fragments of said protein are very well suited for the production of a vaccine. Such proteins or fragments can be obtained from parasites, or from animals or cells infected with Piroplasmid parasites. However, much more convenient is the use of the nucleic acids encoding the Piroplasmid protein according to the invention or an immunogenic fragment of said protein, in an expression system. This is followed by harvesting the proteins or fragments produced and formulating these into a protein subunit vaccine, e.g. by admixing a Piroplasmid protein according to the invention or an immunogenic fragment of said protein, and a pharmaceutically acceptable carrier.

Therefore, yet another aspect of the invention relates to a vaccine comprising a protein according to the invention or an immunogenic fragment of said protein, a nucleic acid, a cDNA fragment, a recombinant DNA molecule, a live recombinant carrier, or a host cell according to the invention, or a combination thereof, and a pharmaceutically acceptable carrier.

As described above, a Piroplasmid protein or an immunogenic fragment of said protein can advantageously be used for vaccination. It serves either to interfere with Piroplasmid parasite proliferation (e.g. inhibition of host cell invasion), or will induce protective immune responses (e.g. specific antibodies or activated lymphocytes) that interfere with parasite proliferation, or the clinical signs it produces.

If such proteins or fragments do not produce the desired response on their own, they can be coupled to a carrier such as KLH, BSA or the like, using techniques known in the art.

The coupling of protein or fragments thereof can also be done to enhance or modify the immune response induced. For instance it is common practice to couple protein(-fragment)s to Tetanus toxoid to enhance the response of T-cells. Also specific effector molecules may be added, such as a toxin, to improve the killing of target cells.

Such couplings can be performed
  chemically, by coupling, conjugation or cross-linking, through dehydration, esterification, etc, of the amino acid sequences either directly or through an intermediate structure.
  physically, by coupling through capture in or on a macromolecular structure, or preferably
  by molecular biological fusion, through the combination of recombinant nucleic acid molecules which comprise fragments of nucleic acid capable of encoding each of the two, such that a single continuous expression product is finally produced.

Such molecular engineering techniques are preferred.

An alternative and efficient way of vaccination is by direct vaccination with DNA encoding the relevant antigen or epitope. Direct vaccination with DNA encoding proteins has been successful for many different proteins, as reviewed in e.g. Donnelly et al. (The Immunologist 1993, vol. 2, p. 20-26). For example in the field of anti-parasite vaccines, protection against e.g. *Plasmodium yoelii* has been obtained with DNA-vaccination with the *P. yoelii* circumsporozoite gene (Hoffman, S. et al. 1994, Vaccine, vol. 12, p. 1529-1533), and protection against *Leishmania major* has been obtained with DNA-vaccination with the *L. major* surface glycoprotein gp63 gene (Xu & Liew 1994, Vaccine, vol. 12, p. 1534-1536).

Such a DNA vaccination can be performed with a nucleic acid, a cDNA fragment, or preferably with a recombinant DNA molecule according to the invention.

Therefore, one preferred embodiment relates to a vaccine according to the invention, characterised in that it comprises a nucleic acid, a cDNA fragment, or a recombinant DNA molecule according to the invention.

Alternatively, a vaccine according to the invention can comprise live recombinant carriers as described above, capable of expressing the Piroplasmid protein according to the invention or immunogenic fragments of said protein. Such vaccines, e.g. based upon a bacterial, a parasitic or a viral carrier or vector have the advantage over subunit vaccines that they better mimic the natural way of infection by Piroplasmida. Also the presentation of the antigens by cells infected with the carriers resembles the route a Piroplasmid protein according to the invention or immunogenic fragments of said protein are presented to the immune system in a natural infection. Moreover, their self-propagation is an advantage since only low amounts of the recombinant carrier are necessary for immunisation.

Thus, another preferred embodiment relates to a vaccine according to the invention, which comprises a live recombinant carrier and a pharmaceutically acceptable carrier.

The host cells as described above can be used to express a Piroplasmid protein according to the invention or an immunogenic fragment of said protein as an expression system. After expression the proteinacious product may be harvested, but alternatively the culture medium or the complete host cells themselves may be used in a vaccine. This has the benefit of omitting purification steps, but of course requires some tolerance by the target mammalians for the media components and/or components of the host cells.

Also within the scope of the invention is a vaccine according to the invention comprising a combination of two or more types of molecules from the Piroplasmid protein according to the invention or an immunogenic fragment of said protein, or a nucleic acid, cDNA, recombinant molecule, live recombinant carrier, or host cells according to the invention. For such vaccines according to the invention the components may be combined in a single dose or in separate doses, and these may be given at the same time or sequentially.

For instance, a combination vaccination of an initial priming with a recombinant DNA plasmid carrying the coding sequence of a Piroplasmid protein, followed some time later by a booster vaccination with a Piroplasmid protein may advantageously be used.

Vaccines according to the invention, can be administered in amounts containing between 0.1 and 1000 μg of a Piroplasmid protein according to the invention or an immunogenic fragment of said protein per mammalian target. Smaller or larger doses can in principle be used; preferably a dose of between 50 and 200 μg of a Piroplasmid protein or an immunogenic fragment thereof is used.

For live viral vector vaccines the dose rate per animal may range from 1 to $10^{10}$ pfu, preferably $10-10^5$ pfu are used.

A pharmaceutically acceptable carrier is understood to be a compound that does not adversely effect the health of the animal to be vaccinated, at least not to the extend that the adverse effect is worse than the effects seen when the animal would not be vaccinated. A pharmaceutically acceptable carrier can be e.g. sterile water or a sterile physiological salt solution. In a more complex form the carrier can e.g. be a buffer.

Often, a vaccine is mixed with stabilizers, e.g. to protect degradation-prone components from being degraded, to enhance the shelf-life of the vaccine, or to improve freeze-drying efficiency. Useful stabilizers are i.a. SPGA (Bovarnik et al. 1950, J. Bacteriology, vol. 59, p. 509), skimmed milk, gelatine, bovine serum albumin, carbohydrates e.g. sorbitol, mannitol, trehalose, starch, sucrose, dextran or glucose, proteins such as albumin or casein or degradation products thereof, and buffers, such as alkali metal phosphates.

The vaccine according to the invention may additionally comprise a so-called "vehicle". A vehicle is a compound to which the proteins, protein fragments, nucleic acids or parts thereof, cDNA's, recombinant molecules, live recombinant carriers, and/or host cells according to the invention adhere, without being covalently bound to it. Such vehicles are i.a. bio-microcapsules, micro-alginates, liposomes, macrosols, aluminium-hydroxide, -phosphate, -sulphate or -oxide, silica, Kaolin®, and Bentonite®, all known in the art.

An example is a vehicle in which the antigen is partially embedded in an immune-stimulating complex, the so-called ISCOM® (EP 109.942, EP 180.564, EP 242.380).

In addition, the vaccine according to the invention may comprise one or more suitable surface-active compounds or emulsifiers, e.g. Span® or Tween®.

Target subjects for the vaccine according to the invention are preferably mammalian, e.g. humans or mammalian animals of veterinary importance. The target may be healthy or diseased, and may be seropositive or -negative for Piroplasmidal parasites or for antibodies to Piroplasmidal parasites. The target subject can be of any age at which it is susceptible to the vaccination.

The more preferred target mammalians for the vaccine according to the invention are bovines, equines, canines, and felines.

The vaccine according to the invention can equally be used as prophylacetic and as therapeutic treatment, and interferes with the establishment and/or with the progression of an infection or its clinical symptoms of disease.

Therefore one aspect of the invention relates to the use of a nucleic acid sequence according to the invention, a cDNA fragment according to the invention, a recombinant DNA molecule according to the invention, a live recombinant carrier according to the invention, or a host cell according to the invention for the manufacture of a vaccine for prophylacetic or therapeutic treatment of an infection or its clinical signs caused by a Piroplasmid organism.

The vaccine according to the invention prevents or reduces the spread of Piroplasmid infection through the population or to the environment.

The vaccine according to the invention can be in several forms, e.g.: a liquid, a gel, an ointment, a powder, a tablet, or a capsule, depending on the desired method of application to the target.

Preferably the vaccine is in the form of an injectable liquid.

The vaccine according to the invention can be administered to the mammalian target according to methods known in the art. For instance by parenteral applications such as through all routes of injection into or through the skin: e.g. intramuscular, intravenous, intraperitoneal, intradermal, submucosal, or subcutaneous. Alternative routes of application that are feasible are by topical application as a drop, spray, gel or ointment to the mucosal epithelium of the eye, nose, mouth, anus, or vagina, or onto the epidermis of the outer skin at any part of the body; by spray as aerosol, or powder. Alternatively, application can be via the alimentary route, by combining with the food, feed or drinking water e.g. as a powder, a liquid, or tablet, or by administration directly into the mouth as a liquid, a gel, a tablet, or a capsule, or to the anus as a suppository.

The preferred application route is by intramuscular or by subcutaneous injection.

It goes without saying that the optimal route of application will depend on the specific particularities of the parasitic infection or clinical disease that is to be prevented or ameliorated, on the characteristics of the vaccine formulation that is used, and on particular characteristics of the target species.

The scheme of the application of the vaccine according to the invention to the target mammalian can be in single or multiple doses, which may be given at the same time or sequentially, in a manner compatible with the dosage and formulation, and in such an amount as will be immunologically effective.

The vaccines of the invention are advantageously applied in a single yearly dose.

In a preferred embodiment, the vaccine according to the invention is characterised in that it comprises an adjuvant.

An adjuvant in general is a substance that boosts the immune response of the target in a non-specific manner. Many different adjuvants are known in the art. Examples of adjuvants are Freund's Complete and -Incomplete adjuvant, vitamin E, non-ionic block polymers and polyamines such as dextransulphate, carbopol and pyran. Also very suitable are saponins, which are the preferred adjuvants. Saponins are preferably added to the vaccine at a level between 10 and 10.000 μg/ml. Within the group of saponins, the saponin Quil A® is the more preferred adjuvant. Saponin and vaccine components may be combined in an ISCOMS® (EP 109.942, EP 180.564, EP 242.380).

Furthermore, peptides such as muramyldipeptides, dimethylglycine, tuftsin, are often used as adjuvant, and mineral oil e.g. Bayol® or Markol®, vegetable oils or emulsions thereof and DiluvacForte® can advantageously be used.

It goes without saying that other ways of adjuvating, adding vehicle compounds or diluents, emulsifying or stabilizing a vaccine are also within the scope of the invention. Such additions are for instance described in well-known handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

The vaccine according to the invention can advantageously be combined with another antigen, or with an immunoactive component. This can also be added in the form of its encoding nucleic acid.

Therefore, in a more preferred embodiment the vaccine according to the invention is characterised in that it comprises an additional immunoactive component or a nucleic acid encoding said additional immunoactive component The additional immunoactive component(s) may be an antigen, an immune enhancing substance, and/or a vaccine; either of these may comprise an adjuvant.

The additional immunoactive component(s) when in the form of an antigen may consist of any antigenic component of human or veterinary importance. It may for instance comprise a biological or synthetic molecule such as a protein, a carbohydrate, a lipopolysaccharide, a nucleic acid encoding a proteinacious antigen, or a recombinant nucleic acid molecule containing such a nucleic acid operably linked to a transcriptional regulatory sequence. Also a host cell comprising such a nucleic acid, a recombinant nucleic acid molecule, or an LRC containing such a nucleic acid, may be a way to deliver the nucleic acid or the additional immunoactive component. Alternatively it may comprise a fractionated or killed microorganism such as a parasite, bacterium or virus.

The additional immunoactive component(s) may be in the form of an immune enhancing substance e.g. a chemokine, or an immunostimulatory nucleic acid, e.g. a CpG motif. Alternatively, the vaccine according to the invention, may itself be added to a vaccine.

For instance a vaccine according to the invention can be combined with a preparation of a *Babesia* subunit vaccine protein, not being a Piroplasmid protein according to the invention or an immunogenic fragment of said protein, to form a combination subunit vaccine against Piroplasmidal infection or associated clinical signs of disease.

Alternatively, the vaccine according to the invention can advantageously be combined with a pharmaceutical component such as an antibiotic, a hormone, or an anti-inflammatory drug.

In an even more preferred embodiment, the vaccine according to the invention is characterised in that said additional immunoactive component or nucleic acid encoding said additional immunoactive component is obtained from an organism infective to: canines: *Ehrlichia canis, Babesia gibsoni, B. vogeli, B. rossi, Leishmania donovani-complex, Canine parvovirus, Canine distemper virus, Leptospira interrogans serovars canicola, icterohaemorrhagiae, pomona, grippotyphosa, bratislava,* Canine hepatitis virus, Canine parainfluenza virus, rabies virus, *Hepatozoon canis* and *Borrelia burgdorferi*; to bovines: Bovine Herpes virus, Bovine Viral Diarrhoea virus, Parainfluenza type 3 virus, Bovine Paramyxovirus, Foot and Mouth Disease virus, *Pasteurella haemolytica,* Bovine Respiratory Syncytial Virus, *Theileria* sp., *Babesia* sp., *Trypanosoma* sp., *Anaplasma* sp., *Neospora caninum, Staphylococcus aureus, Streptococcus agalactiae, Mycoplasma, E. coli, Enterobacter, Klebsiella, Citrobacter, Cryptosporidium, Salmonella* and *Streptococcus dysgalactiae*; and to equines: *Streptococcus equi, Streptococcus zooepidemicus, Rhodococcus equi, Corynebacterium pseudotuberculosis, Pseudomonas mallei, Actinobacillus equii* and *Pasteurella multocida.* Potomac fever agent, *Clostridium tetanii, Mycobacterium pseudomallei,* Vesicular Stomatitisvirus, Borna disease virus, Equine influenza virus, African horse sickness virus, Equine arteritis virus, Equine herpes virus 1-4, Infectious anaemia virus, Equine encephalomyelitis virus and Japanese B encephalitis virus.

The Piroplasmid protein according to the invention, or the immunogenic fragment of said protein, the nucleic acid, cDNA, recombinant molecule, live recombinant carrier, and/or the host cells according to the invention for the first time allow the efficient generation of specific antibodies against a Piroplasmid protein, or an immunogenic fragment of said protein. This makes the vaccine according to the invention suitable as marker vaccine, as it allows the differentiation between parasite infected and -vaccinated mammalian targets, through methods known in the art.

Alternatively, these specific antibodies may be used as a vaccine themselves, for so called "passive vaccination".

Therefore another aspect of the invention relates to a vaccine, characterised in that it comprises an antibody against a protein according to the invention, or an antibody against an immunogenic fragment of said protein, or a combination thereof, and a pharmaceutically acceptable carrier.

The antibody may be of natural or synthetic origin. The antibody may be in the form of an antiserum or a purified antibody. Such purified antibodies can advantageously be obtained from an expression system.

Methods for large-scale production of antibodies according to the invention are also known in the art. Such methods rely on the cloning of (fragments on the genetic information encoding the protein according to the invention in a filamentous phage for phage display. Such techniques are described i.a. at the "Antibody Engineering Page" under "filamentous phage display" at http://aximt1.imt.uni-marburg.de/~rek/aepphage.html., and in review papers by Cortese, R. et al., (1994) in Trends in Biotechn., vol. 12, p. 262-267; by Clarckson, T. & Wells, J. A. (1994) in Trends in Biotechn., vol. 12, p. 173-183; Marks, J. D. et al., (1992) J. Biol. Chem., vol. 267, p. 16007-16010; Winter, G. et al., (1994) Annu. Rev. Immunol., vol. 12, p. 433-455, and by Little, M. et al., (1994) Biotechn. Adv., vol. 12, p. 539-555.

The phages are subsequently used to screen camelid expression libraries expressing camelid heavy chain antibodies. (Muyldermans, S. and Lauwereys, M., Journ. Molec. Recogn., vol. 12, 131-140 (1999) and Ghahroudi, M. A. et al., FEBS Letters, vol. 414, p. 512-526 (1997)). Cells from the library that express the desired antibodies can be replicated and can subsequently be used for large-scale expression of antibodies.

A combination in a vaccine of an antigen 'loaded' with antibodies against that antigen is known in the art as a "complex" vaccine. Such vaccines according to the invention may advantageously be used.

For reasons of e.g. stability or economy the Piroplasmid protein according to the invention or immunogenic fragments of said protein, or nucleic acids, cDNA's, recombinant molecules, live recombinant carriers, host cells or vaccines according to the invention may be freeze-dried. In general this will enable prolonged storage at temperatures above zero °C., e.g. at 4° C.

Procedures for freeze-drying are known to persons skilled in the art; equipment for freeze-drying at different scales is available commercially.

Therefore, in a most preferred embodiment, the vaccines according to the invention are characterised in that said vaccines are in a freeze-dried form.

To reconstitute a freeze-dried vaccine, it may be suspended in a physiologically acceptable diluent. Such a diluent can e.g. be as simple as sterile water, or a physiological salt solution. In a more complex form it may be suspended in an emulsion as outlined in PCT/EP99/10178.

Still another aspect of the invention relates to a method for the preparation of a vaccine according to the invention, said method comprising the admixing of a protein according to the invention or an immunogenic fragment of said protein, a nucleic acid, a cDNA fragment, a recombinant DNA molecule, a live recombinant carrier, or a host cell according to the invention, or a combination thereof, and a pharmaceutically acceptable carrier.

Yet another aspect of the invention relates to a method for the preparation of a vaccine according to the invention, said method comprising the admixing of an antibody against a protein according to the invention or an antibody against an immunogenic fragment of said protein, or a combination thereof, and a pharmaceutically acceptable carrier As outlined above, a vaccine obtainable by the methods according to the invention can equally be used as prophylacetic and as therapeutic treatment, and will interfere both with the establishment and/or with the progression of an infection or its clinical signs of disease.

Therefore, a further aspect of the invention relates to the use of a protein according to the invention or an immunogenic fragment of said protein, for the manufacture of a vaccine for prophylacetic or therapeutic treatment of an infection or its clinical signs caused by an organism of the Piroplasmida.

Again a further aspect of the invention relates to a diagnostic test for the detection of a nucleic acid associated with a Piroplasmid organism, characterised in that the test comprises a nucleic acid, said nucleic acid being at least 70%, preferably 75%, more preferably 80, 85, 90, 92, 94, 95, 96, 97, 98, 99, or 100% In that order of preference, similar to the nucleic acid sequence depicted in SEQ ID NO: 1, 3, 5, 7, or 9 or a nucleic acid that is complementary to said nucleic acid, wherein either of the nucleic acids have a length of at least 15 nucleotides, preferably 17, more preferably 18, 19, 20, 24, 28, 32, 35 or 40 nucleotides, in that order of preference.

Yet a further aspect of the invention relates to a diagnostic test for the detection of antibodies against a Piroplasmid organism, characterised in that said test comprises a protein according to the invention or an immunogenic fragment of said protein, or a combination thereof.

For instance BIIA1 or BIIA2 or an immunogenic fragment of either is coupled to a solid phase carrier, this is incubated with a sample to be tested, is washed, and presence of bound antibodies is detected. Preferred diagnostic method is by ELISA.

Still a further aspect of the invention relates to a diagnostic test for the detection of antigenic material from a Piroplasmid organism, characterised in that said test comprises an antibody against a protein according to the invention or an antibody against an immunogenic fragment of said protein, or a combination thereof.

For instance antibodies against BIIA1 or BIIA2 or an Immunogenic fragment of either are coupled to a solid phase carrier, this is incubated with a sample to be tested, is washed, and presence of bound protein is detected. Preferred diagnostic method is by ELISA.

The invention will now be further described with reference to the following, non-limiting, examples.

EXAMPLES

Example I 1.1. Techniques Used 1.1.1. *B. bovis* In vitro Culture

*B. bovis* Israel isolate (clonal line C61411) was cultured in vitro as previously described (Levy & Ristic 1980, Science, vol. 207, p. 1218-1220). Briefly, *B. bovis* cultures were maintained in 24-well plates (1.2 ml total volume) or in 25 cm$^2$ bottles (15 ml total volume) containing medium M199 (Cambrex Bioscience, Belgium), with 40% bovine serum (from an adult donor cow), 50 µgml$^{-1}$ Gentamicin (Gibco BRL), 25 mM sodium bicarbonate, and bovine erythrocytes at 5% packed cell volume (PCV). Cultures were incubated at 37° C., 5% $CO_2$ in air, and parasitaemia was kept between 1% and 12% by daily dilution.

*B. bovis* Mexico isolate (clonal line-C9.1) was cultured according to the same protocol as used for clonal line C61411 (Israel isolate) except that cultures were maintained at 90% $N_2$, 5% $CO_2$, 5% $O_2$ instead of 5% $CO_2$ in air.

1.1.2. Construction of *B. bovis* Genomic and cDNA Library

A cDNA library was constructed from 5 µg *B. bovis* mRNA using the λZAP-cDNA® Synthesis Kit (Stratagene) according to the manufacturer's instructions. cDNA fragments of 0.5 to 4 kb were collected by gel filtration on a sepharose CL4B column and ligated into the EcoRI/XhoI site of λ uniZAP-XR Express vector. Giga pack III Gold was used for packaging into phage particles followed by transformation of *Escherichia coli* XL-1 Blue MRF'cells. 1.2×10$^6$ plaques were obtained of which an amplified library was made.

Single-pass sequence runs were performed on 15000 cDNA clones that were automatically picked at random from the plated cDNA library to establish an EST dataset. From this EST dataset a database consisting of 12892 high quality sequences (476 bp average length) was constructed.

For constructing the genomic library, 600 µg of *B. bovis* DNA was partially digested with EcoRI (150 units or 250 units) for 1 h at 37° C. The digested DNA was size fractionated on a Sepharose CL-4B column. Fragments of 0.5 kb to 8 kb were ligated into the EcoRI site of λ-ZAPII-Express, packaged using Gigapack III Gold Packaging extract and transformed in *E. coli* XL 1-Blue MRF'competent cells. 2.5×10$^8$ plaques were obtained of which an amplified library was made.

The cDNA libraries were screened with a probe produced through PCR with primers specific for BIIA1 or for BIIA2.

1.1.3. Screening of *B. bovis* Genomic and cDNA Library for the Genes for BIIA1 and BIIA2

The *B. bovis* genomic and cDNA libraries were screened to isolate clones for the genes of BIIA1 and BIIA2 with a specific probe made by PCR. Specific primers used were: for the BIIA1 gene:

```
primer 1:
5'- CCACGGCTCTGGAATCTATGTC -3'        (SEQ ID NO: 11)

(SEQ ID NO: 12)
primer 2:
5'- CAAAAGGATACCTATATTTGGTAC -3',
``` and for the BIIA2 gene:

```
                                      (SEQ ID NO: 13)
primer 3:    5'- TGTGGTAGATGAATCTGCTAGTATATC -3'

(SEQ ID NO: 14)
primer 4:    5'- CTATGCCACGGCATTCAGCAACATTTA -3'
```

Both primer pairs were used to amplify a fragment from a clone from the EST database of *B. bovis*, by PCR in a 50 µl volume containing 0.2 mM dNTP, 20 pmol/µl of each primer, 100 ng *B. bovis* total genomic DNA and 0.5 U Taq DNA polymerase in standard buffer (Promega). Amplification was performed for 30 cycles with the conditions for the BIIA1 probe at: 92° C. for 30 s, 58° C. for 30 s, and 72° C. for 30 s, and for the BIIA2 probe at: 95° C. for 1 min, 58° C. for 1 min, and 72° C. for 10 min. These cycles were preceded by initial denaturation for 3 min at 95° C. and a final elongation at 72° C. for 10 min.

Both probes were purified from agarose gel and labelled with 50 µCi $^{32}$P-dATP (3000 Ci/mmol), using a Random Primer labelling kit (Roche). In total $4.10^6$ cDNA and $4.10^5$ genomic DNA library plaques were screened by standard procedures (Sambrook & Russell, supra) for cloning the BIIA1 cDNA; whereas $5.10^5$ cDNA and an equal number of genomic DNA library plaques were screened for cloning the BIIA2 cDNA. After 2 cycles of plaque purification all clones were in vivo excised for isolation of the phagemid inserts as described in the manufacturer's instructions (Stratagene) and sequenced on both strands, using automated cycle sequencing with the dye terminator method (ABI PRISM® dye terminator kit, Pharmacia).

To obtain the full-length BIIA1 and BIIA2 cDNA's, the non-coding 5'-ends were identified with 5'-RACE (GeneRacer™ kit, Invitrogen; L1502-01, according to the manufacturer instructions). The obtained full length clones were inserted into pCR2.1 cloning plasmids and sequenced on both strands, as described above. The resulting sequences are presented in SEQ ID NO: 1 (BIIA1) and SEQ ID NO: 5 (BIIA2).

1.1.4. Expression of Recombinant BIIA1 in *E. coli*

The clones of BIIA1 en BIIA2 were subcloned by PCR from the pCR2.1 cloning plasmids.

The primers used for subcloning BIIA1 were:

```
                                          (SEQ ID NO: 15)
primer 5:    5'- CCCGGATCCATGCAGTTACATAACAAA -3'

(SEQ ID NO: 16)
primer 6:    5'- GGGAAGCTTCTGAGCAAAGGAAATAGG -3'
```

These primers for BIIA1 introduced a BamHI restriction enzyme site prior to base 1 (numbered from the first base of the initiation codon) and a HindIII site after base 1504.

The primers used for subcloning BIIA2 were:

```
                                          (SEQ ID NO: 17)
primer 7:    5'- CCCGAATTCGTGGTAGATGAATCTGCT -3'

(SEQ ID NO: 18)
primer 8:    5'- CCCGTCGACTGCCTCGCCCCAAATGTTGT -3'
```

These primers for BIIA2 introduced an Eco RI site, and a Sal I site.

Figure 2:
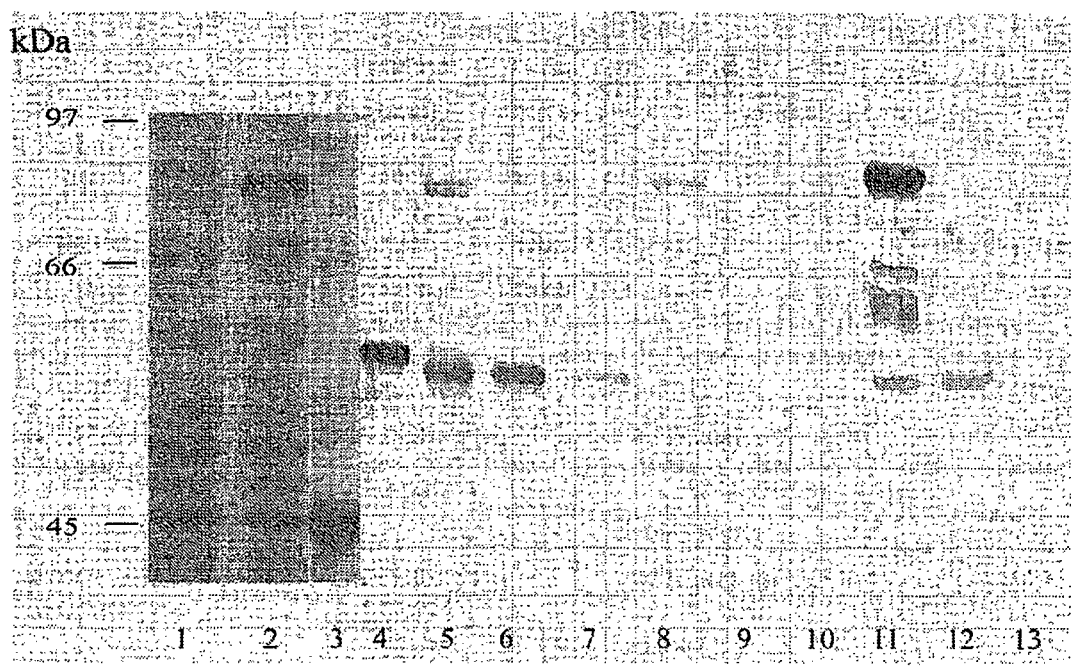

After PCR (30 cycles of 1 min 94° C., 1 min 55° C., 1 min 72° C.), the fragments were gel purified, annealed to pET-32a vector and used for transformation in *E. coli* NovaBlue® strain. Plasmids containing the appropriate insert were used to transform in expression host strains, BL21 (DE3). Fusion proteins with thioredoxin were obtained with maximal yield after induction with 1 mM of isopropyl-β-D thiogalactosidase (IPTG) for 4 hr at 37° C. as shown by analysis of total cell samples at 0 and 4 hr after induction. Bacterial pellets were boiled at 95° C. in SDS-polyacrylamide (SDS-PAGE) sample buffer containing 2% (v/v) β-mercaptoethanol, run on 10% SDS-PAGE minigels, and Coomassie Brilliant Blue stained to confirm expression (FIGS. 1 and 2).

1.1.5. Peptide Selection and Generation of Monospecific Antiserum

After the BIIA1 and BIIA2 genes were completely sequenced, peptides were selected from computer-translated sequences, for induction of specific polyclonal antibodies through immunisation of test animals.

The sequence analysis program Protean of DNA Star® was used to select peptide regions that have a good surface probability and contained charged alpha amphipathic regions.

Peptides selected from BIIA1 (SEQ ID NO: 2) were:

```
peptide 1:              cysteine-AFHKEPNNRRLTKRS,
aa numbers 46-60:

peptide 2:              cysteine-RGVGMNWATYDKDSG,
aa numbers 395-409:

peptide 3:              cysteine-YVEPRAKNTNKYLDV.
aa numbers 453-467:
```

Peptides selected from BIIA2 (SEQ ID NO: 6) were:

```
peptide 4:              cysteine-PGKRTRALLDLRMIE,
aa numbers 255-269:

peptide 5:              cysteine-RVGNTDEEHNHRKDMD,
aa numbers 424-439:

peptide 6:              cysteine-VYDDHPEESENTGIN.
aa numbers 547-561:
```

After the synthesis of the peptides, they were coupled to a carrier protein: Maleimide activated keyhole limpet haemocyanin (KLH) (Pierce; 77605) according to the manufacturer's instructions. The peptide-carrier conjugate was used to generate rabbit polyclonal antisera.

For that purpose three groups of NZW-rabbits (each group contained 2 rabbits) were immunized five times subcutaneously with a 3-week interval between consecutive immunizations. Before the immunisation blood serum was collected of each rabbit, which was used as negative control. Each rabbit was injected with 250 µg peptide coupled to KLH that was taken up in an equal volume of adjuvant Stimune® (ID-DLO, Lelystad, the Netherlands). Total volume that was injected in each rabbit was 1000 µl. Sera were tested periodically for reactivity by ELISA. Plasmaforeses were done one week after the last immunization and sera were collected.

1.1.6. ELISA

The antibody response was evaluated by ELISA. Ninety-six-well microtiter plates were coated with 150 ng of either peptide 1 or peptide 2 per well, incubated 30 min at 37° C., blocked for 1 h with PBS/BSA. Consecutive dilutions (1:50 to 1:50.000) of individual rabbit sera were incubated for 1 h at 37° C. The plates were washed, and 1:2000 diluted swine anti rabbit HRP-conjugated secondary antibody was Incubated for 1 h. The plates were washed and developed for 45 min with ABTS [2,2'-azinobis(3-ethylbenzthiazolinesulfonic acid)]-peroxidase substrate (Roche biochemicals). The $OD_{405}$ was recorded, and comparative ELISA titres were calculated.

1.1.7. Immunofluorescence Assay

The recognition of *B. bovis* merozoites by anti-sera against peptides from BIIA1 and BIIA2 was tested by indirect immunofluorescence assay (IFA). Thin blood smears were fixed with chilled methanol. Primary incubation with polyclonal rabbit anti-BIIA1 (1:40) or polyclonal mouse anti-BIIA1 (1:5 to 1:160) for 30 min was followed by three wash steps of 5 min. Slides were incubated with 1:80 goat anti-rabbit immunoglobulin G (IgG) fluorescein isothiocyanate-labelled antibodies (Nordic) for 30 min. The slides were washed again, and Vectashield® solution (Vector laboratories) was applied, objects were covered with a cover-glass and visualized on a UV fluorescence microscope with FITC filters (450-480/515-565 nm). IFA titres were determined as the last serum dilution with a positive recognition of the parasite compared to the negative pre-immune serum diluted 1:5.

1.1.8. Preparation of Total Merozoite Protein Extracts and Proteins Solubilised Upon Invasion 800 µl samples of merozoites, prepared as described above for in vitro invasion, were partially separated from erythrocyte ghosts by filtration over 1.2 µM polypropylene prefilters (Millipore, AN1202500). Filtered merozoites were pooled and washed twice in 20 volumes of PBS containing 25 mM sodium bicarbonate (pH 8.0) followed by centrifugation at 2000 g for 20 min at 4° C. After the second wash the pellet was resuspended in an equal volume of PBS (pH 8.0) and divided in aliquots of 200 µl that were centrifuged (10.000×g, 5 min at 4° C.) and stored as 100 µl cell pellets ($2 \times 10^9$ merozoites) at −20° C. after removal of supernatant. Frozen merozoite pellets were thawed just before use and lysed, reduced and alkylated by using a Proteoprep® membrane extraction kit (Sigma) according the manufacturer's instructions and finally obtained in 1.7 ml of buffer compatible with direct application on SDS-polyacrylamide gels or iso-electrofocussing (IEF) strips. Insoluble material was removed by centrifugation at 16.000×g for 3 min at 4° C. Protein concentration was determined by the Bradford method (Anal. Biochem. 1976, vol. 72, p. 248-254). As the extracts contained considerable amounts of erythrocyte proteins, control extracts were prepared in the same way but starting with a culture of non-infected erythrocytes.

Proteins solubilised upon invasion were obtained by gently removing the overlaying buffer after 1 h of in vitro invasion as described above. The samples were centrifuged (2000×g, 10 min, 4° C.) after which the pellet (which was invisible) was discarded and the supernatant centrifuged again at high speed for removal of membrane fragments (20 min, 12.000×g, 4° C.). The final supernatant was dialysed (Pierce; Snakeskin® pleated dialysis tubing, 68035) overnight against 10 mM $KHPO_4$, pH 7.5. Residual haemoglobin was removed batch-wise by incubating 50 ml of the dialysed supernatant with 6.5 ml DEAE sepharose fast flow (Amersham Biosciences) equilibrated in dialysis buffer for 90 min at 4° C. on a rotating platform. The suspension was centrifuged for 5 min at 3000×g at 4° C. after which the DEAE sepharose washed 4 times by addition of 50 ml of dialysis buffer followed by centrifugation for 5 min at 3000×g at 4° C. Bound proteins were eluted by addition of 6 ml of elution buffer (350 mM KCl, 10 mM $KHPO_4$, pH 7.5) and incubation for 5 min followed by centrifugation for 5 min at 3000×g at 4° C. The supernatant was concentrated and de-salted over 10 kDa filters (YM-10, Millipore).

1.1.9. SDS-polyacrylamide Electrophoresis and Western Blotting

Proteins were resolved in the presence or absence of β-mercaptoethanol and were separated on a 10% SDS-PAGE and electrophoretically transferred to an Immobilon™-P membrane (Millipore). The blot was blocked with 5% skimmed milk diluted in 0.5% Tween® 20 containing phosphate-buffered saline (PBST) for 1 h at 37° C. An appropriate dilution (1:500) of primary antibody in 2% skimmed milk in PBST was incubated for 1 h overnight. The blot washed with PBST and then incubated with a 1:10.000 dilution of anti-rabbit-horseradish peroxidase (HRP)-conjugated secondary antibody (DAKO) for 1 h at 37° C. After being washed with PBST, the blot was developed with TMB MB substrate kit (Lucron Bioproducts BV; KPL 50-77-00) or with enhanced chemoluminescence (ECL)+ (Amersham; RPN2132).

1.1.10. Iso-electric Focusing

Total merozoite extract, invasion supernatant, and BIIA1 protein samples were resuspended in rehydration solution (7 M urea, 2 M thiourea, 4% CHAPS, 2% carrier ampholyte mixture pH 4-7NL (IPG buffer and 20 mM DTT). BIIA2 protein samples were separated in the first dimension using carrier ampholyte mixture pH 3-10NL. IEF instrumentation, IPG gels and reagents used were from Amersham Biosciences, unless otherwise indicated. 35 µg total merozoite protein or 35 µg invasion supernatant with protease inhibitor (Complete, Roche) was loaded on 7 cm strips (pH 4-7NL). For 13 cm strips, 150 µg of total merozoite proteins or 150 µg invasion supernatant was loaded. Strips were rehydrated (10-14 h) and focused overnight (14-17 h) in an automated run (1 min 300 V, 90 min during which the voltage rose to 3500 V, followed by continued focusing at 3500 V, to a total of 35-40 KVh, on IPGPhor™).

Following iso-electric focussing, the proteins were reduced and bound to SDS by equilibrating each strip for 15 min in 10 ml of SDS equilibration buffer (50 mM Tris, 6M urea, 2% SDS, 30% glycerol, pH 8.8) containing 30 mM DTT (added fresh before use). A second equilibration step in SDS equilibration buffer containing 2.5% iodoacetamide (also freshly added) instead of dithiotreitol, was performed in order to prevent protein reoxidation and to minimise reactions of cysteine residues.

The second-dimensional SDS gel electrophoresis gel was carried out in a Hoefer SE600 system. Silver staining was used to visualise proteins after 2-D electrophoresis. Images of the gels were acquired using LabScan® v3.0 software on a Umax flatbed scanner and were analysed using ImageMaster® 2D v3.01 software (Amersham Biotech). For immune blotting, proteins on 7 cm strips were separated on a 10% SDS-PAGE gel or 13 cm strips were separated on 2-D protein gel and transferred to an Immobilon™-P membrane (Millipore; IPVH00010). The procedure followed for two-dimensional blots was the same as that for the 1-D blots.

1.1.11. B. bovis In vitro Invasion Assay

Invasion was performed as described previously (Fransen et al. 2003, Microbes Infect. vol. 5, p. 365-372), with slight modifications. B. bovis infected red blood cells at 6 to 8% parasitaemia, were centrifuged at 2000×g, 10 min, 15° C., and resuspended in an equal volume of VyMs buffer (Vega & Martinez, see Fransen, supra). 800 µl samples were submitted to five intermittent (10 seconds, at 0° C. in between pulses) high voltage pulses (2.5 kV, 200Ω, 25 µF) in 4 mm BioRad cuvettes (165-2088) using a BioRad Gene Pulser® with pulse controller.

8 ml of PBS containing 25 mM sodiumbicarbonate (pH 8.0, 20° C.) was added to each 800 µl sample followed by centrifugation (1800×g) for 10 min at 15° C. A second, identical wash was performed except that centrifugation was done at 1300×g after which the merozoite pellet was resuspended in 800 µl PBS containing 25 mM sodiumbicarbonate (pH 8.0, 20° C.). Invasion was initiated by addition of 1 volume of resuspended merozoites to 9 volumes of suspended bovine erythrocytes (5.5% PCV in PBS pH 8.0 containing 25 mM sodiumbicarbonate, pre-incubated for 30 min at 37° C. in $CO_2$ in air) and was performed in 24-well plates (final volume 1.2 ml), in 25-cm² flasks (15 ml) or in 80 cm² flasks (50 ml) at 37° C., 5% CO₂ in air. Giemsa-stained slides were prepared after 1 h and parasitisised erythrocytes out of a total of 5000 erythrocytes were counted.

1.1.12. In vitro Inhibition of Invasion by Polyclonal Rabbit Antisera

200 µl of B. bovis merozoites, liberated by high voltage pulsing and resuspended in PBS containing 25 mM sodium-bicarbonate (pH 8.0) as described above, were incubated with 40 µl of rabbit antisera for 1 h at 20° C. After 1 h, 960 µl of suspended bovine erythrocytes (6.25% PCV in PBS pH 8.0 containing 25 mM sodiumbicarbonate, pre-incubated for 30 min at 37° C. in CO₂ in air) were added, followed by 1 h of incubation after which Giemsa-stained slides were prepared and counted to determine the level of invasion. The rabbit antisera used were raised against synthetic peptides derived from the BIIA1 and BIA2 amino acid sequence and a control serum raised against an unrelated control peptide (YAGRLF-SKRTAATAYKLQ). Peptides had been linked to keyhole limpet haemocyanin (KLH) prior to immunization. Pre-immune sera were also included in the test.

1.2. Results of Example 1

1.2.1. Identification and Cloning of a Full Length cDNA Encoding BIIA1 and BIIA2

Probing the B. bovis cDNA library with PCR probes (350 bp for BIIA1 and 450 bp for BIIA2), resulted in the cloning and sequencing of a 2181 bp cDNA for BIIA1 and of 2385 bp for BIIA2. Both contained an open reading frame and a 3' non-coding region terminating in a polyA-tail. To determine the 5' capped end of the full-length mRNA's, total mRNA was dephosphorylated after which the 5' caps, which are left intact, were removed by tobacco acid pyrophosphatase followed by ligation of a specific RNA oligonucleotide. Subsequently, nested PCR on first strand cDNA allowed the cloning and sequencing of a fragment representing the 5' end of the B. bovis mRNA for BIIA1 and for BIIA2.

Translation by computer of the 1815 bp ORF of BIIA1 predicted a 67.2 kDa; translation of the 1965 bp ORF for BIIA2 predicted a 65.6 kDa protein.

1.2.2. Recognition of Recombinant BIIA1 and BIIA2 by Antisera Against Derived Peptides.

To enable further studies on the BIIA proteins, rabbits were immunized with KLH-linked synthetic peptides 1-6 (supra). All antisera specifically recognized a recombinant fusion product of thioredoxin and the part of the BIIA proteins that was expressed in E. coli BL21 cells (FIGS. 1 and 2). Polyacrylamide gel electrophoresis of total cell lysates obtained before (lane 1) and after (lane 2) induction with IPTG identified the recombinant fusion product for BIIA1 and for BIIA2. Rec BIIA1 and BIIA2 both are recognized by all three immune sera (lanes 5, 8, 11) and not by pre-immune sera (lanes 6, 9, 12) on immuno-blots. Immune recognition was specific for the BIIA part of the fusion product as a control protein, a recombinant fusion product of B. bovis rab5 (lane 3, Asp-5 to Lys-208, GenBank Acc. No.: 324137.1) expressed in PET32a was not recognized (lanes 7, 10, 13) by these sera. Also, immune recognition was peptide specific and not due to antibodies induced by the KLH carrier protein used for Immunization as antiserum raised against a KLH-linked synthetic peptide unrelated to BIIA1 or BIIA2 did not recognize the BIIA1 recombinant fusion product (lane 13).

1.2.3. Immunofluorescence Microscopy

Figure 3:
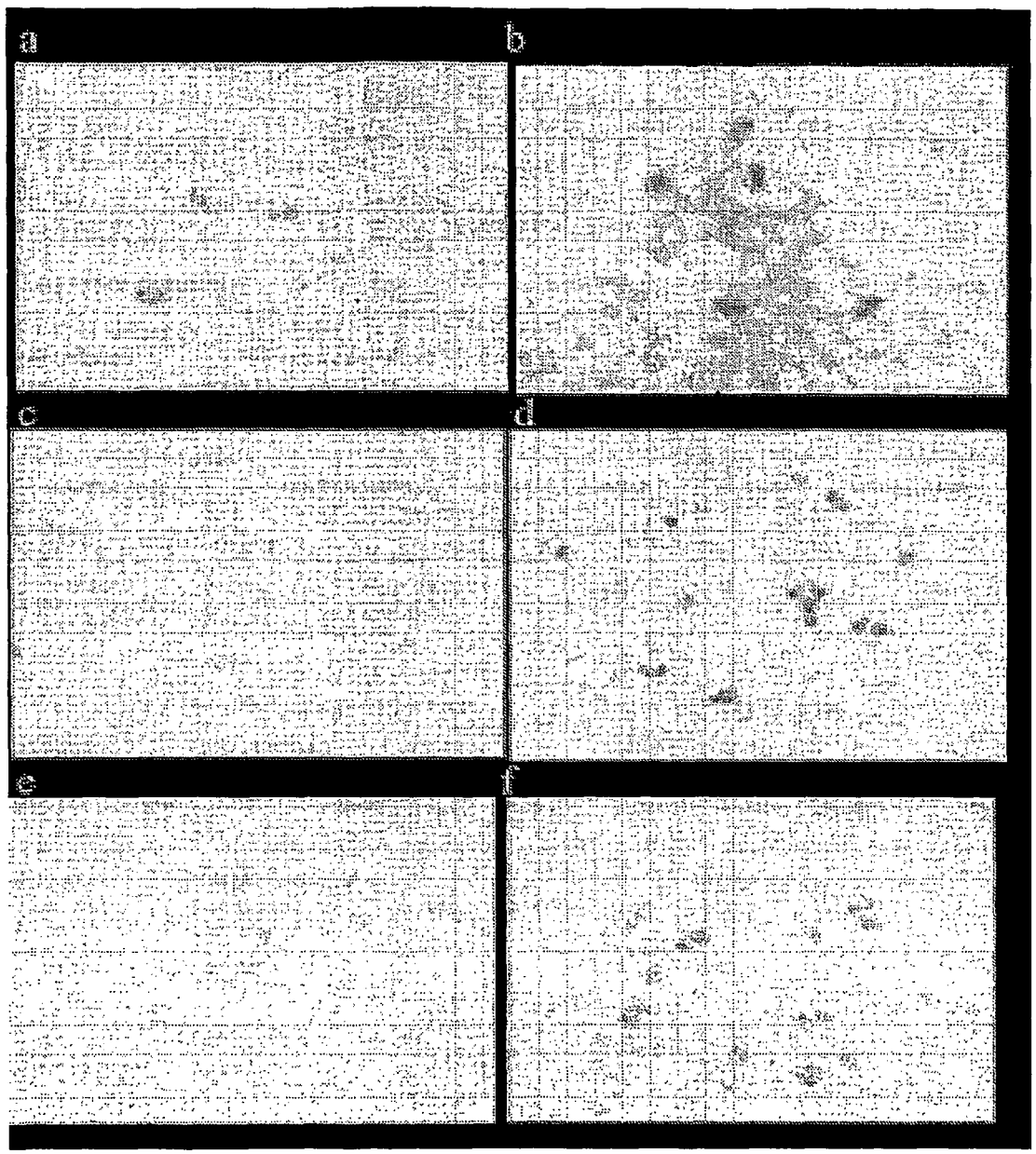
Figure 4:
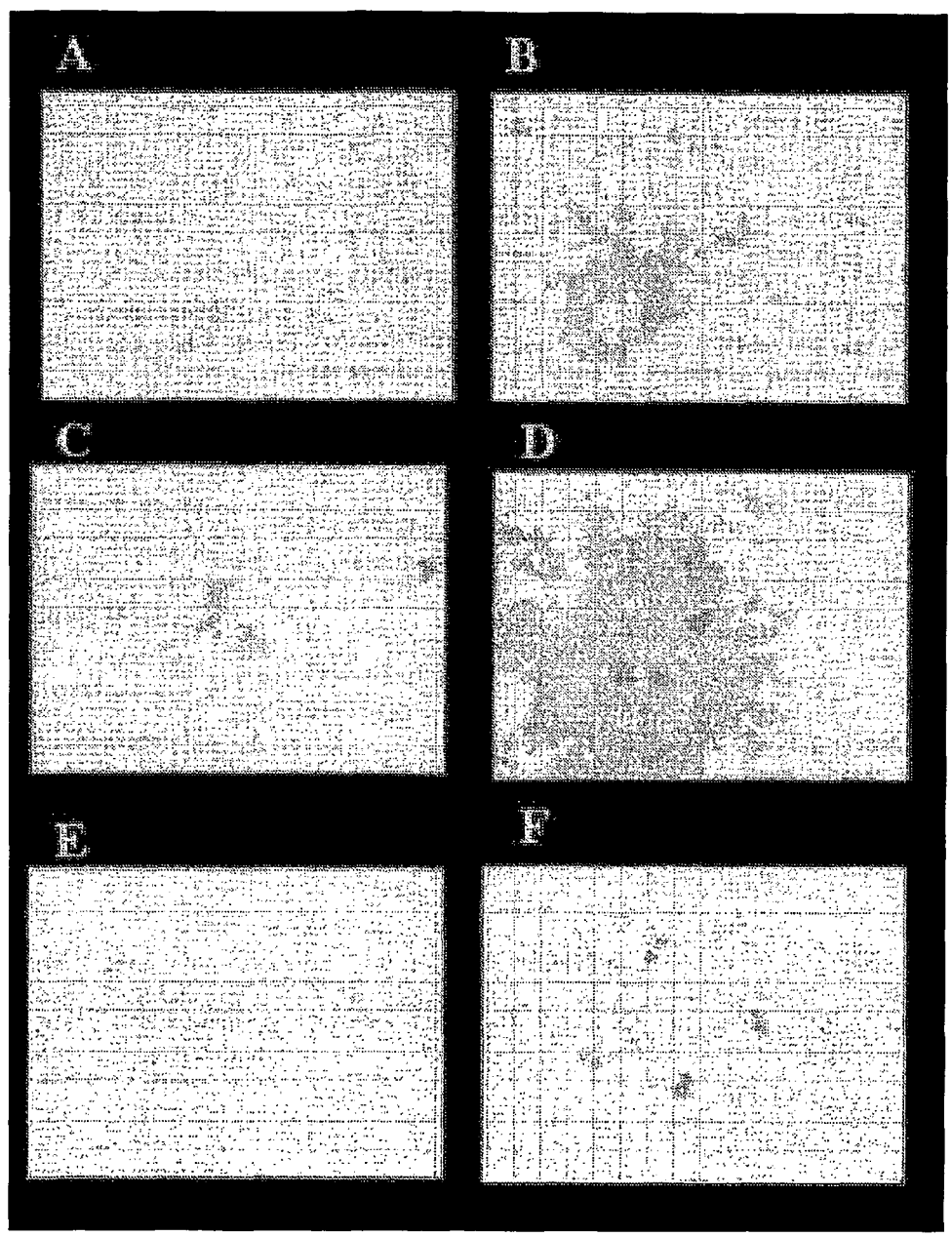

To localize the BIIA proteins in the parasite, immunofluorescence studies using rabbit antisera against the six KLH-linked peptides of BIIA1 and BIIA2 were performed on B. bovis in vitro cultures attached to glass slides by methanol fixation (FIGS. 3 and 4). Incubation with pre-immune sera (panels A, C, E) did not result in any specific staining of parasites above a background signal of faint fluorescence derived from infected as well as non-infected erythrocytes. In contrast, immune sera resulted in specific staining of parasites in any microscope field examined (panels B, D, F). Fluorescent parasites were detectable with antisera against all three peptides at a dilution of 1:5. Although intra-erythrocytic B. bovis parasites and free merozoites are small (±1 by 2 µm) a maximal magnification allowed a clear visualization of the staining pattern.

1.2.4. Inhibition of In vitro Invasion by Peptide-Specific Antisera

Figure 5:
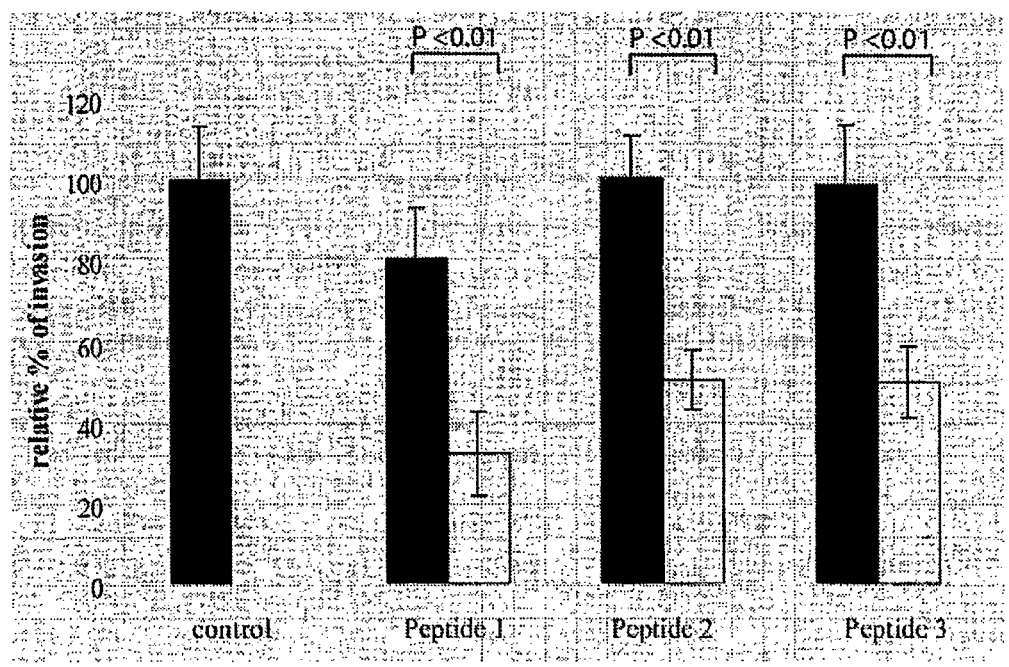
Figure 6:
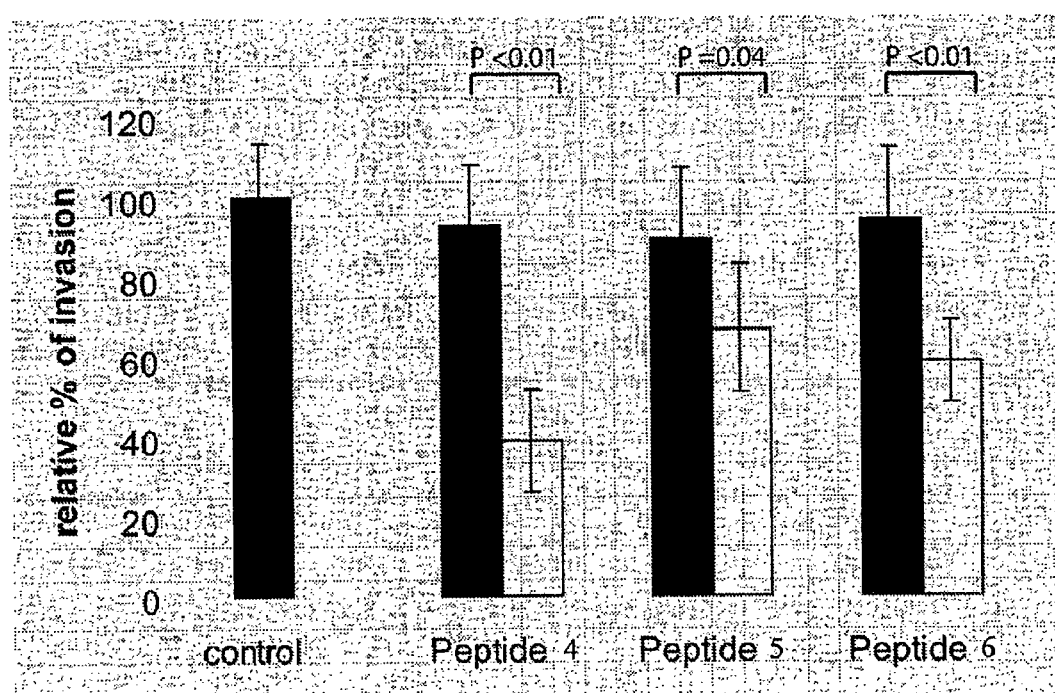

A B. bovis in vitro invasion assay, allowing the study of the invasion of erythrocytes by free merozoites in a protein free buffer within a time span of 1 h, was used to assess the effect of antisera directed against the 6 peptides derived from different domains of BIIA1 and BIIA2. Free merozoites were pre-incubated for 1 h at 20° C. with the anti-peptide antisera and with the control serum directed against a non-related peptide after which Invasion was started by the addition of erythrocytes. All antisera against the BIIA peptides gave rise to significant inhibition of invasion whereas pre-immune sera and control antiserum had no significant effect on invasion efficiency (FIGS. 5 and 6). For BIIA1, the strongest effect of 65±10% inhibition of invasion was observed by the antiserum directed against peptide 1; for BIIA2, the strongest effect of 70±10% inhibition of invasion was observed by the antiserum directed against peptide 4.

1.2.5. Mapping BIIA Proteins on 2-D-Gels

Figure 7:
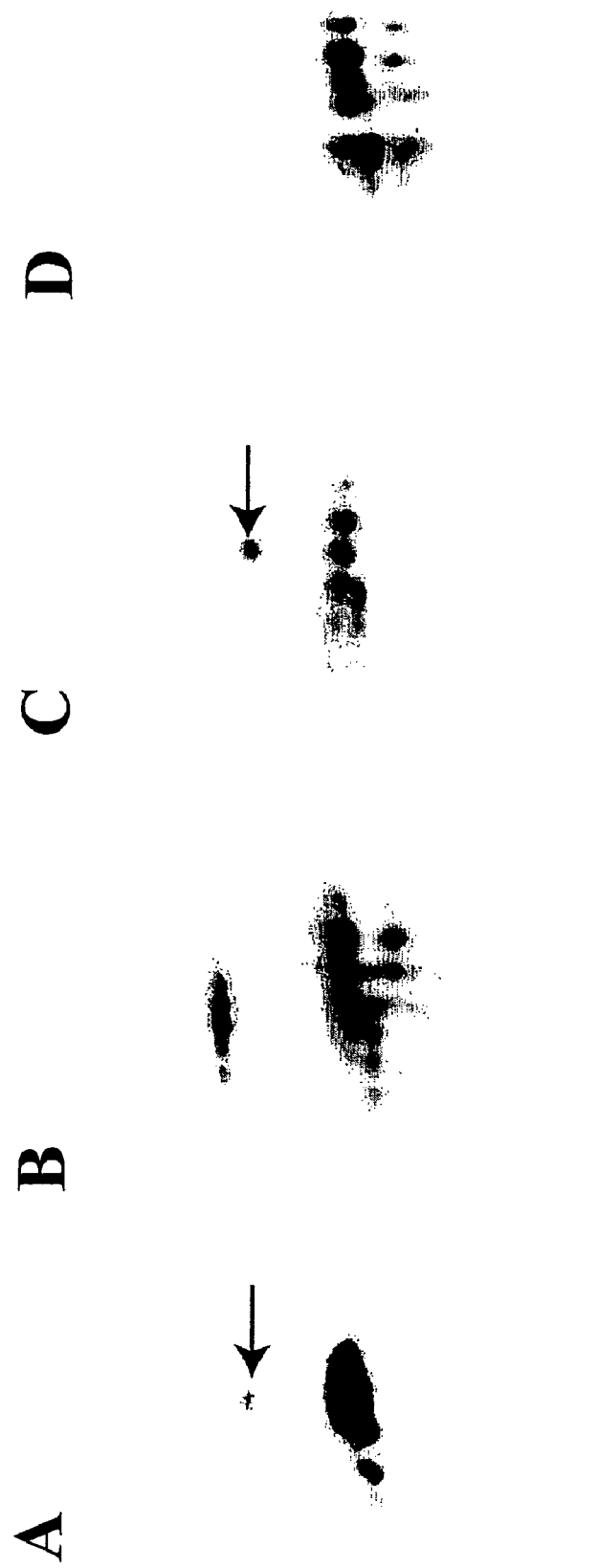
Figure 8:
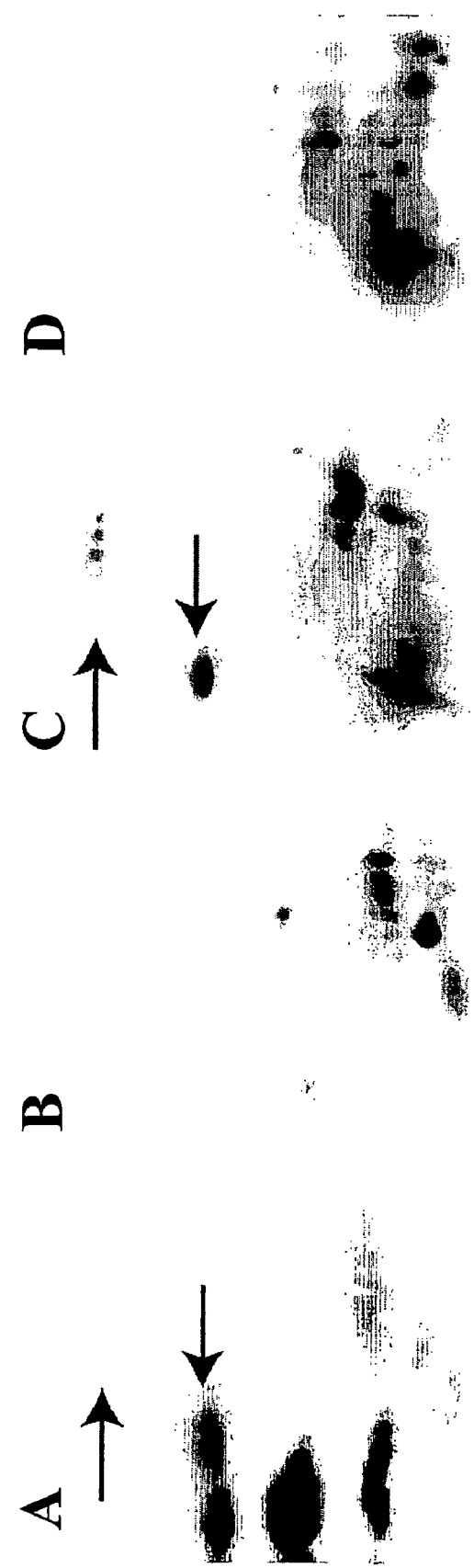
Figure 9:
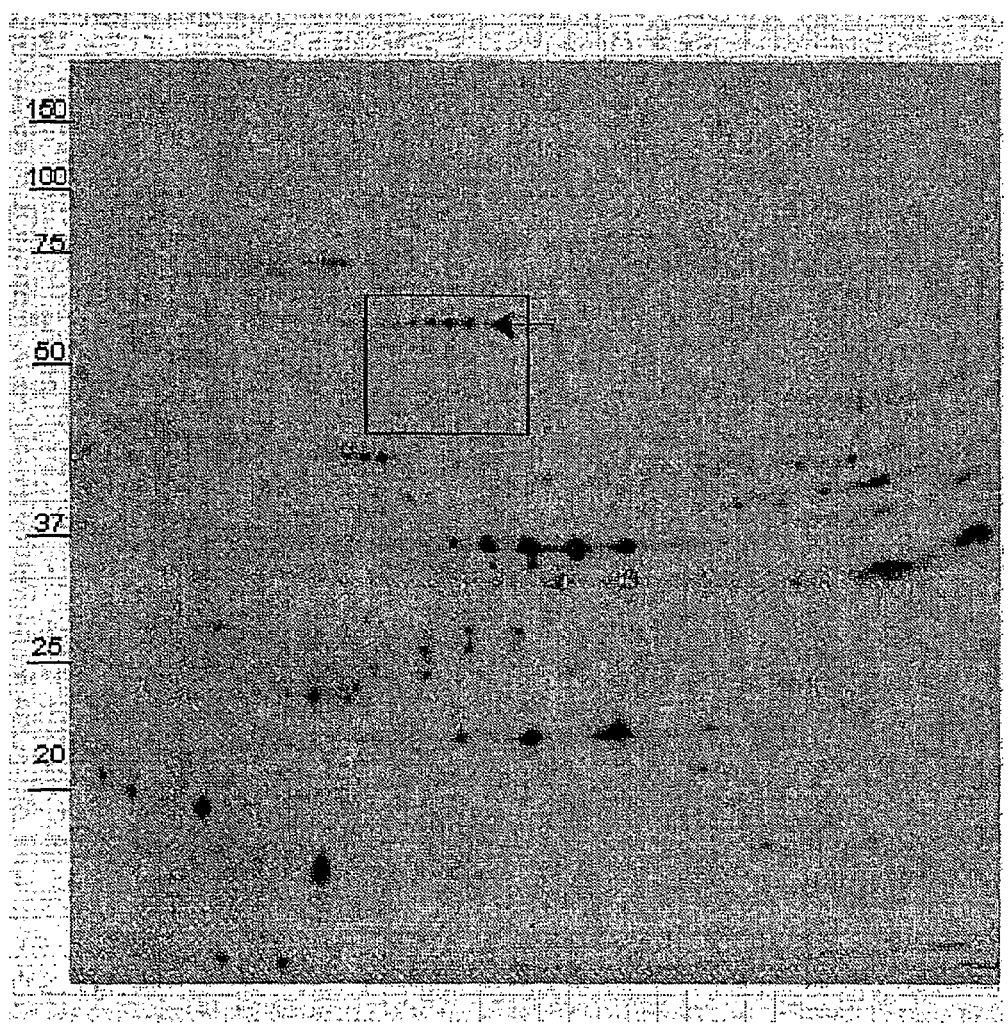

To determine whether BIIA1 and BIIA2 become exposed in the medium as soluble proteins during invasion of erythrocytes, thus constituting part of the SPA mentioned above, immunoblotting of invasion supernatants was performed. BIIA1 and BIIA2 were localized on two-dimensional immunoblots. 50 µg of concentrated invasion supernatant was separated by iso-electrofocussing followed by electrophoresis on SDS-polyacrylamide gels. Proteins were blotted on PVDF membranes. Excised parts of the membranes (45 to 90 kDa) were incubated with anti-BIIA1 peptide antisera against peptides 1 or 3 (FIG. 7, panels A and C respectively) as well as with anti-BIIA2 peptide antisera against peptides 4 and 6 (FIG. 8, panels A and C respectively). For both proteins, antibodies against peptides 1 and 4, were bound to the same specific spots (arrows) in addition to a-specific staining of proteins that were also present on control blots. These had been prepared from supernatants of uninfected red blood cells (RBC) prepared under identical conditions but in absence of merozoites (FIGS. 7 and 8, panels B and D). Spots localized by immunoblotting were subsequently matched to a silver-stained 2-D-protein gel of a similar sample that was obtained from a parallel experiment in which use was made of parasites that were metabolically labelled with ³⁵S-Met prior to invasion. FIG. 9 displays the pattern obtained after exposure to film showing exclusively proteins of B. bovis as erythrocyte proteins have not incorporated label. By using imaging software, the spots detected by immunoblotting with anti-BIIA1-peptide antisera could be matched to a row of ±70 kDa spots on the autoradiograph and on the silverstained gel (see arrows on FIG. 9). BIIA2 is represented by spots of minor intensity indicating a lower abundance of the native protein.

Example II

Cloning, Expression and Characterisation of BIIA3

Total amplified DNA from the *B. bovis* cDNA library described in § 1.1.2 was screened for the BIIA3 gene with the following primers:

```
                                          (SEQ ID NO: 19)
primer 9:   5'- CCCGAATTCCATGATGGTGAAGTTCCACAC -3'

(SEQ ID NO: 20)
primer 10:  5'- CCCGTCGACGTTGGCCCCCTTTCGGTGAT -3'
```

PCR was performed as described in § 1.1.3.

The PCR fragment was sequenced directly; the resulting sequence is presented in SEQ ID NO: 9 (BIIA3).

The PCR fragment of the BIIA3 cDNA was cloned into expression vetor pET-32a, as described in § 1.1.4. Primers 9 and 10 provided Eco RI and Sal I restriction sites.

The computer-translated sequence of the BIIA3 protein is presented in SEQ ID NO: 10. The 1635 nucleotide ORF in the BIIA3 cDNA encodes a 61.0 kDa protein.

Peptides were predicted from this protein for induction of specific antibodies in test animals, as described in § 1.1.5.

Peptides selected from BIIA3 protein are:

```
peptide 7:          cysteine - GELKKLSDNIPTKMP,
aa numbers 122-136 peptide 8:          cysteine - SGSARVETSLESSVP.
aa numbers 385-399
```

The peptides were coupled to KLH, and used to generate rabbit polyclonal antibodies as described in § 1.1.5. Rabbit sera were evaluated by ELISA, as described in §1.1.6.

Figure 10:
Figure 10:
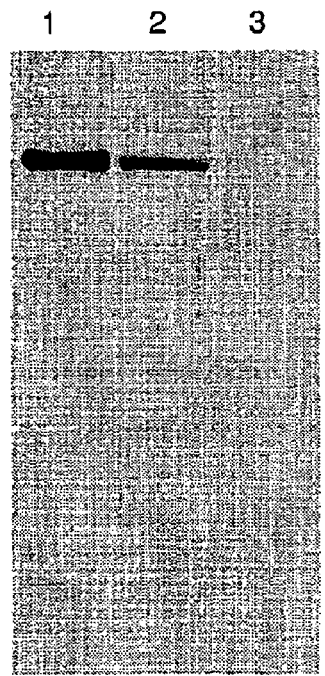

The rabbit polyclonal anti-peptide antisera were to detect recBIIA3 (*E. coli* expressed thioredoxin fused BIIA3 protein) in 1-D Western blot. The results are depicted in FIG. 10, panel A: Rec BIIA3 was recognized by antisera against both peptides 7 and 8, whereas preimmune sera did not recognize Rec BIIA3.

Polyclonal antiserum against BIIA3 (and against BIIA1 and BIIA2) was raised in cattle, as described in Example III.

This bovine antiserum was also used in a 1-D Western blot on recBIIA3. Results are depicted in FIG. 10, panel B: serum from two animals recognised recBIIA3, whereas pre-immune bovine serum did not.

Figure 11:
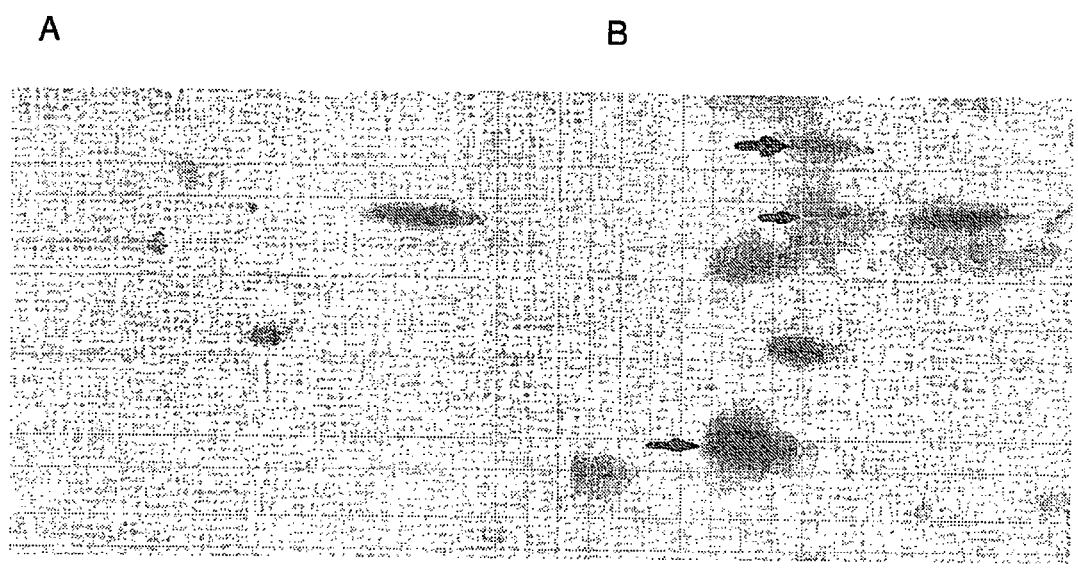

The bovine antiserum against recBIIA3 was also used on a 2-D gel of native *B. bovis* proteins as described in § 1.1.8 and 1.1.9. Results are shown in FIG. 11.

Preimmune bovine serum reacted with several spots of red blood cell origin (panel A). For panel B sepharose column purified recBIIA3-immune IgG was used. This specifically recognised (groups of) spots of ~95 kDa, ~75 kDa and ~30 kDa (see arrows). Apparently, processed and multimeric forms of native BIIA3 are also recognised.

Figure 12:
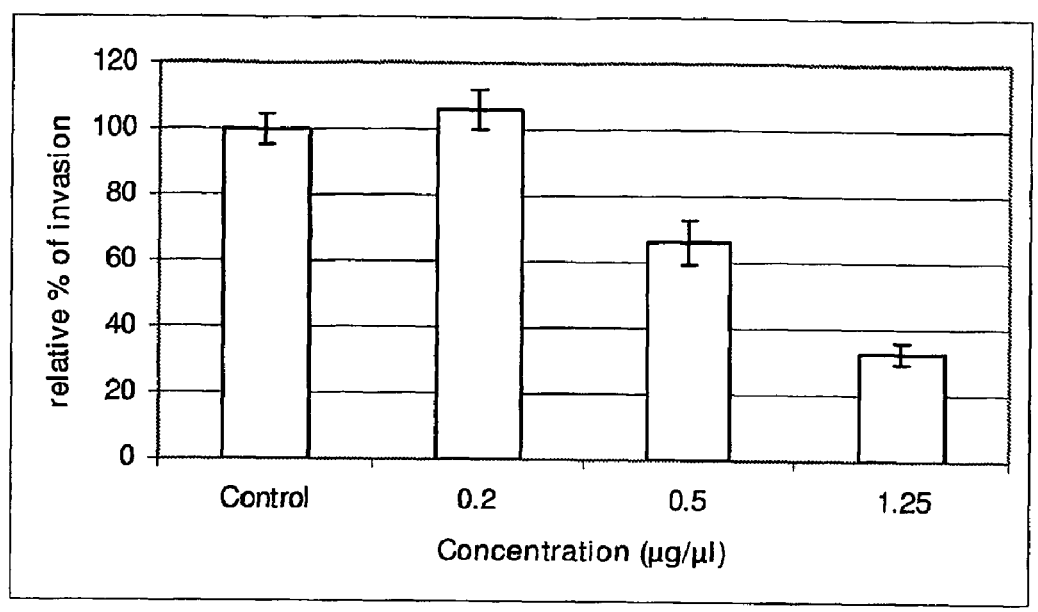

The rabbit polyclonal antiserum against peptide 7 was demonstrated to have invasion inhibiting properties, see FIG. 12. Sepharose G purified IgG was used at three different concentrations, leading to a maximum inhibition of 65%. Non-immune IgG, and PBS did not result in inhibition (Control column).

Rabbit polyclonal antiserum directed against peptide 7 was also used to determine the subcellular localization of BIIA3 in *B. bovis* merozoites in the infected erythrocyte, by indirect immunofluorescence. Detection was by multiphoton microscopy.

Thin blood smears were fixed in acetone for 10 min and air-dried. Primary incubation with anti peptide 7 rabbit serum (1:20) for 30 min was followed by three wash steps of 5 min with PBS. Slides were then incubated with goat anti-rabbit IgG conjugated with Alexa 488 (20 µg/ml, Molecular Probes Inc., Eugene, USA) for 30 min and washed with PBS. Subsequently, for dual labeling, the slides were incubated with DAPI (0.5 µM, Molecular Probes Inc.) for 20 min and washed. Fluor Save® solution was applied and the slides were left overnight at room temperature, covered, in a horizontal position.

Fluorescent signals were visualized using a Bio-Rad Radiance 2100 MP confocal and multi-photon system equipped with a Nikon TE300 inverted microscope. Excitation of the DAPI probes was achieved by multi-photon excitation at 780 nm using a mode-locked Titanium-Sapphire laser (Tsunami, Spectra-Physics) pumped by a 10 W solid state laser (Milennia Xs, Spectra-Physics), while the Alexa 488 probe was excited by an Argon laser at 488 nm.

The multiphoton IFT results showed BIIA3 specific staining was present in the apical region of the *Babesia parasite*.

Example III

Generation and Use of Bovine Antisera Against Recombinant BIIA1, BIIA2, and BIIA3

Recombinant expression products of BIIA1, BIIA2, and BIIA3 were generated in *E. coli* as described in section 1.1.4. Bacteria were pelleted and solubilized in 6 M Guanidinium HCl. The total cell lysate was centrifuged at 9000 rpm for 10 min, and the soluble lysate was bound to a suspension of Ni-NTA agarose in GuHCL. Beads were washed three times with 8M Urea, and specific antigen was subsequently eluted with 250 mM imidazol in 3M Urea.

Each vaccine dose contained 100 µg purified recBIIA antigen and was formulated with saponin adjuvant in a 2 ml final dose. Vaccines were applied intramuscular in the neck of immunological competent cattle, each group numbered 5 animals. 5 weeks after the priming a booster vaccination was given with the same formulation. 3 weeks after the booster blood was taken and serum was prepared for analysis.

Purification of bovine specific IgG was performed by incubating 5 ml of antiserum with 2 ml of GammaBind Plus® Sepharose (Amersham-biosciences) for 1 h at 20° C. in binding buffer (0.01 M Sodiumphosphate pH 7.4, 0.15 M Nacl, 0.01 M EDTA). The column was washed with binding buffer and IgG was eluated 5 ml 0.5 M NaAc pH 3.0, and immediately neutralised with Tris HCl pH 9.0. IgG was concentrated and dialysed against PBS pH 7.4.

In vitro invasion inhibition by total IgG purified from bovine antisera raised against recombinant BIIA1, BIIA2 and BIIA3 (cloned from Israel strain) was performed as described for polyclonal rabbit antisera (§ 1.1.11 and 1.2.4) using final bovine IgG concentrations of 0.15 µg/µl or 0.75 µg/µl during preincubation. All tests were performed twice using antibodies of two different animals for each antigen. The results shown in FIG. 13 display the combined data of the individual antisera per antigen. Standard deviation is indicated. To show the inhibition is also effective on invasion of a heterologous *Babesia strain*, a clonal line (C9.1) derived from a Mexican isolate (M07) of *B. bovis* was tested.

The effectivity of the Inhibition of erythrocyte invasion by both *Babesia* strains is comparable. Effectivity of BIIA1 and BIIA2 (between 3 and 12%) seemed even higher than that of BIIA3 (23-25%).

LEGEND TO THE FIGURES

FIG. 1:
Lane 1: pET-BIIA1 before induction with IPTG.
Lane 2: pET-BIIA1 4 h after induction with IPTG.
Lane 3: pET-Rab5 4 h after induction.
Lanes 4, 5, 6 incubated with anti-peptide 1;
Lanes 7, 8, 9 incubated with anti-peptide 2;
Lanes 10, 11, 12 incubated with anti-peptide 3.
Lanes 4, 7, 10 contain pET-BIIA1 4 h after induction, incubated with pre-immune sera;
Lanes 5, 8, 11 the same as in lanes 4, 7, and 10, but incubated with immune sera.
Lanes 6, 9, 12 contain pET-Rab5 4 h after induction incubated with immune sera.
Lane 13: pET-BIIA1 4 h after induction, and incubated with antiserum again KLH-linked peptide unrelated to *B. bovis*.

FIG. 2:
Lane 1: pET-BIIA2 before induction with IPTG.
Lane 2: pET-BIIA2 4 h after induction with IPTG.
Lane 3: pET-Rab5 4 h after induction.
Lanes 4, 5, 6 incubated with anti-peptide 4;
Lanes 7, 8, 9 incubated with anti-peptide 5;
Lanes 10, 11, 12 incubated with anti-peptide 6.
Lanes 4, 7, 10 contain pET-BIIA2 4 h after induction, incubated with pre-immune sera of rabbits;
Lanes 5, 8, 11 the same as in lanes 4, 7, and 10, but incubated with immune sera.
Lanes 6, 9, 12 contain pET-Rab5 4 h after induction, incubated with immune sera.
Lane 13 contains pET-BIIA2 4 h after induction, and incubated with antiserum again KLH-linked peptide unrelated to *B. bovis*.

FIG. 3:
Panels A, C and E display methanol-fixed in vitro cultures of *B. bovis* incubated with pre-immune rabbit antisera against peptides 1, 2 and 3 of BIIA1 respectively. Panels B, D, F are similar to A, C and E but Incubated with the corresponding immune sera. For reproductive purposes the colours have been inverted.

FIG. 4:
Panels A, C and E display methanol-fixed in vitro cultures of *B. bovis* Incubated with pre-immune rabbit antisera against peptide 4, 5 and 6 of BIIA2 respectively. Panels B, D, F are similar to A, C and E but incubated with the corresponding immune sera. For reproductive purposes the colours have been inverted.

FIG. 5:
Control columns represent a pre-incubation with antiserum against a non-related peptide that gave no inhibition. Antisera (open bars) as well as pre-immune rabbit sera (black bars) against peptides 1, 2 and 3 of BIIA1 were tested twice in triplo.

FIG. 6:
Control columns represent a pre-incubation with antiserum against a non-related peptide that gave no inhibition. Antisera (open bars) as well as pre-immune sera (black bars) against peptides 4, 5 and 6 of BIIA2 were tested twice in triplo.

FIG. 7:
Panels A and C: 2-D-immunoblots with immune serum against BIIA1 peptides 1 and 3 respectively. Panels B and D: 2-D-immunoblots with pre-immune serum of rabbits immunized with peptides 1 and 3 of BIIA1 respectively. Arrows indicate spots specific for antisera against peptide 1 as well as peptide 3.

FIG. 8:
Panels A and C: 2-D-immunoblots with immune serum against BIIA2 peptides 4 and 6 respectively. Panels B and D: 2-D-immunoblots with pre-immune serum of rabbits immunized with peptide 4 and 6 of BIIA2 respectively. Arrows indicate spots specific for antisera against peptide 4 as well as peptide 6.

FIG. 9:
Autoradiograph of a 2-D gel as used for the immunoblots presented in FIGS. 7 and 8, displaying only *B. bovis* derived proteins that were labelled with $^{35}$S-Met by metabolic labelling prior to invasion. Arrows indicate the spots that have been identified as BIIA1 by matching with immunoblots shown in FIG. 7 using imaging software.

FIG. 10:
1-D Western blot of *E. coli* expressed recBIIA3, recognized by polyclonal rabbit antisera raised against peptides 7 and 8.
Panel A: rabbit anti-peptide antisera: lane 1: anti-peptide 7; lane 3: anti-peptide 8; both in serum dilution 1:2000.
Lanes 2 and 4: pre-immune sera of both peptide-antisera rabbit donors.
Panel B: Bovine anti-recBIIA3 antisera: lanes 1, and 2: purified immune IgG in 1:200.000 from two animals; lane 3, pre-immune bovine serum.

FIG. 11:
2-D Western blot of native *B. bovis* proteins recognized by bovine polyclonal antiserum directed against recBIIA3.
Panel A: pre-immune bovine serum.
Panel B: Sepharose G purified immune IgG, at 0.8 μg/ml. Arrows indicate BIIA3 specific antibody recognition.

FIG. 12:
Invasion inhibition assay of rabbit polyclonal anti-peptide 7 immune IgG, inhibiting the invasion of *B. bovis* Israel isolate into bovine erythrocytes.
Inhibition by control (pre-immune serum) was set to 100%.
Horizontal axis: concentration of purified immune IgG; vertical axis: relative % of invasion inhibition efficacy, with standard deviation (n=3).

Figure 13:
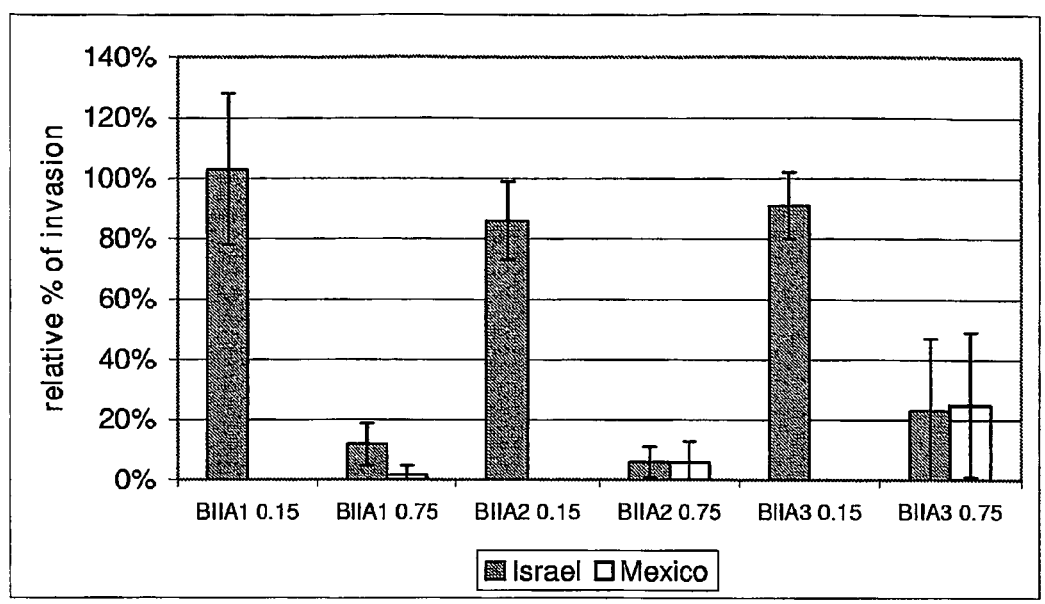

FIG. 13:
Invasion inhibition assay of bovine polyclonal immune IgG against *E. coli* expressed recBIIA1, recBIIA2, and recBIIA3, inhibiting the invasion of *B. bovis* isolates from Israel and from Mexico into bovine erythrocytes.
Inhibition by control (pre-immune serum) was set to 100%.
Horizontal axis: final IgG concentration in μg/μl; vertical axis: relative % of invasion inhibition efficacy, with standard deviation (n=2×2).

The invention claimed is:

1. An isolated protein comprising an amino acid sequence selected from the group consisting of:
   SEQ ID NO: 2 and
   immunogenic fragments of SEQ ID NO: 2,
wherein said protein elicits the production of antibodies that interfere with invasion by *Babesia bovis* into erythrocytes.

2. An isolated nucleic acid wherein said nucleic acid encodes the protein according to claim 1.

3. The nucleic acid of claim 2, wherein the nucleic acid is cDNA.

4. An isolated recombinant DNA molecule comprising the nucleic acid according to claim 2 under the control of a functionally linked promoter.

5. An isolated recombinant DNA molecule comprising the cDNA according to claim 3 under the control of a functionally linked promoter.

6. An isolated live recombinant carrier comprising the isolated nucleic acid of claim 2.

7. An isolated live recombinant carrier comprising the isolated nucleic acid of claim 3.

8. An isolated live recombinant carrier comprising the isolated recombinant DNA molecule of claim 4.

9. An isolated live recombinant carrier comprising the isolated recombinant DNA molecule of claim 5.

10. An isolated host cell comprising the isolated nucleic acid of claim 2.

11. An isolated host cell comprising the isolated nucleic acid of claim 3.

12. An isolated host cell comprising the isolated recombinant DNA molecule of claim 4.

13. An isolated host cell comprising the isolated recombinant DNA molecule of claim 5.

* * * * *

SEQUENCE LISTING

<160> NUMBER OF SEQ ID NOS: 20

<210> SEQ ID NO 1
<211> LENGTH: 1818
<212> TYPE: DNA
<213> ORGANISM: Babesia bovis
<220> FEATURE:
<221> NAME/KEY: CDS
<222> LOCATION: (1)..(1818)

<400> SEQUENCE: 1

```
atg cag tta cat aac aaa atg cag tca act tct ctc aaa tat aac tac        48
Met Gln Leu His Asn Lys Met Gln Ser Thr Ser Leu Lys Tyr Asn Tyr
1               5                   10                  15 aag cgc atg ctt tgt atg gct ctt gta cca gtt atc tta tcg tca ttt        96
Lys Arg Met Leu Cys Met Ala Leu Val Pro Val Ile Leu Ser Ser Phe
            20                  25                  30 ttt gcg gaa gat gct tta gct tcc aac tcc acg ctt ttc gct ttc cac       144
Phe Ala Glu Asp Ala Leu Ala Ser Asn Ser Thr Leu Phe Ala Phe His
        35                  40                  45 aag gaa cca aac aat cgt agg ctt acc aaa agg tct tca aga gga cag       192
Lys Glu Pro Asn Asn Arg Arg Leu Thr Lys Arg Ser Ser Arg Gly Gln
    50                  55                  60 ttg ctc aac tca agg agg ggt tcg gat gat gcg tcc gaa tct tcc gat       240
Leu Leu Asn Ser Arg Arg Gly Ser Asp Asp Ala Ser Glu Ser Ser Asp
65                  70                  75                  80 aga tac cca ggt agg tcg ggt ggc tct aag aat tcg agc caa tcc ccc       288
Arg Tyr Pro Gly Arg Ser Gly Gly Ser Lys Asn Ser Ser Gln Ser Pro
                85                  90                  95 tgg atc aag tat atg caa aag ttc gac att ccc cgt aac cac ggc tct       336
Trp Ile Lys Tyr Met Gln Lys Phe Asp Ile Pro Arg Asn His Gly Ser
            100                 105                 110 gga atc tat gtc gat ctt gga gga tat gaa tcc gtt ggt tca aaa agt       384
Gly Ile Tyr Val Asp Leu Gly Gly Tyr Glu Ser Val Gly Ser Lys Ser
        115                 120                 125 tat cgt atg ccc gtt ggt aag tgc cca gta gtc ggt aaa att ata gac       432
Tyr Arg Met Pro Val Gly Lys Cys Pro Val Val Gly Lys Ile Ile Asp
    130                 135                 140 ctt gga aat ggt gcc gac ttc ctc gat ccc att tca tca gac gac cca       480
Leu Gly Asn Gly Ala Asp Phe Leu Asp Pro Ile Ser Ser Asp Asp Pro
145                 150                 155                 160 agt tac cgt ggt ttg gca ttc ccc gag act gct gtg gac tct aat att       528
Ser Tyr Arg Gly Leu Ala Phe Pro Glu Thr Ala Val Asp Ser Asn Ile
                165                 170                 175 ccc aca caa cca aag aca cgt ggt tct tca tca gca tct gcg gcc aaa       576
Pro Thr Gln Pro Lys Thr Arg Gly Ser Ser Ser Ala Ser Ala Ala Lys
            180                 185                 190 tta tct cct gtt tcg gcg aaa gat ctg aga cgt tgg gga tat gaa ggt       624
Leu Ser Pro Val Ser Ala Lys Asp Leu Arg Arg Trp Gly Tyr Glu Gly
        195                 200                 205 aat gat gta gcg aat tgc tca gaa tat gct agt aac ctc att ccc gca       672
Asn Asp Val Ala Asn Cys Ser Glu Tyr Ala Ser Asn Leu Ile Pro Ala
    210                 215                 220 tca gac agg agt acc aaa tat agg tat cct ttt gtt ttt gac agt gat       720
Ser Asp Arg Ser Thr Lys Tyr Arg Tyr Pro Phe Val Phe Asp Ser Asp
225                 230                 235                 240 aac cag atg tgt tac ata ctg tac tct gcc ata caa tac aac caa gga       768
Asn Gln Met Cys Tyr Ile Leu Tyr Ser Ala Ile Gln Tyr Asn Gln Gly
                245                 250                 255
```

```
                                                                    -continued aat agg tat tgt gac aac gat ggt agc tcc gaa gat ggt aca agc tct      816
Asn Arg Tyr Cys Asp Asn Asp Gly Ser Ser Glu Asp Gly Thr Ser Ser
        260                 265                 270 ttg ctt tgc atg aaa cct tac aag agc gct gag gat gca cac tta tac      864
Leu Leu Cys Met Lys Pro Tyr Lys Ser Ala Glu Asp Ala His Leu Tyr
275                 280                 285 tac ggt tct gcg aaa gtt gac ccc gat tgg gaa gaa aat tgt ccc atg      912
Tyr Gly Ser Ala Lys Val Asp Pro Asp Trp Glu Glu Asn Cys Pro Met
        290                 295                 300 cac ccg gta agg gat gcc att ttt ggt aaa tgg tct ggt ggc tct tgt      960
His Pro Val Arg Asp Ala Ile Phe Gly Lys Trp Ser Gly Gly Ser Cys
305                 310                 315                 320 gtt gcc att gct cct gca ttc caa gaa tat gcc aac agc act gaa gac     1008
Val Ala Ile Ala Pro Ala Phe Gln Glu Tyr Ala Asn Ser Thr Glu Asp
                325                 330                 335 tgt gca gcc att tta ttc gat aac tct gca act gac ttg aat atc gaa     1056
Cys Ala Ala Ile Leu Phe Asp Asn Ser Ala Thr Asp Leu Asn Ile Glu
        340                 345                 350 gct gtt aac gaa gat ttt aat gaa ctt aaa gaa ttg acc gat ggg ctt     1104
Ala Val Asn Glu Asp Phe Asn Glu Leu Lys Glu Leu Thr Asp Gly Leu
                355                 360                 365 aaa aga ttg aac atg tcg aag gtt gca aac gct att ttt tct ccc ctc     1152
Lys Arg Leu Asn Met Ser Lys Val Ala Asn Ala Ile Phe Ser Pro Leu
370                 375                 380 tcc aat gtt gca ggt acc agt cga att tca cgt ggt gtg ggt atg aac     1200
Ser Asn Val Ala Gly Thr Ser Arg Ile Ser Arg Gly Val Gly Met Asn
385                 390                 395                 400 tgg gct aca tac gat aaa gat tct ggt atg tgt gct ctc att aac gaa     1248
Trp Ala Thr Tyr Asp Lys Asp Ser Gly Met Cys Ala Leu Ile Asn Glu
                405                 410                 415 aca cct aac tgc ttg atc ttg aac gcg gga agc att gct ctc acg gct     1296
Thr Pro Asn Cys Leu Ile Leu Asn Ala Gly Ser Ile Ala Leu Thr Ala
        420                 425                 430 ata ggt tca cct ctc gag tat gac gct gtt aac tat cct tgc cac atc     1344
Ile Gly Ser Pro Leu Glu Tyr Asp Ala Val Asn Tyr Pro Cys His Ile
                435                 440                 445 gac acc aat ggt tac gtt gag cca cgt gca aag aat acc aac aaa tac     1392
Asp Thr Asn Gly Tyr Val Glu Pro Arg Ala Lys Asn Thr Asn Lys Tyr
        450                 455                 460 ctt gat gtt cct ttc gag gtc aca act gct ttg agc atg aag aca cta     1440
Leu Asp Val Pro Phe Glu Val Thr Thr Ala Leu Ser Met Lys Thr Leu
465                 470                 475                 480 aaa tgc gat gcc tat gtt cac acc aag tac tct gac agt tgt ggt acc     1488
Lys Cys Asp Ala Tyr Val His Thr Lys Tyr Ser Asp Ser Cys Gly Thr
                485                 490                 495 tat ttc ctt tgc tca gac gtc aaa cct aac tgg ttc att agg ttc tta     1536
Tyr Phe Leu Cys Ser Asp Val Lys Pro Asn Trp Phe Ile Arg Phe Leu
        500                 505                 510 cac atg atc gga ctc tac aac aca aag cgt atc gta ata ttc gtg tgc     1584
His Met Ile Gly Leu Tyr Asn Thr Lys Arg Ile Val Ile Phe Val Cys
        515                 520                 525 tgt acc act acc gcc atc gtt ctc act atc tgg ata tgg aaa cga ttc     1632
Cys Thr Thr Thr Ala Ile Val Leu Thr Ile Trp Ile Trp Lys Arg Phe
530                 535                 540 atc aag gct aag aaa gag ccg gcc cct cca agt ttc gac aaa tac cta     1680
Ile Lys Ala Lys Lys Glu Pro Ala Pro Pro Ser Phe Asp Lys Tyr Leu
545                 550                 555                 560 agc aac tat gat tat gat aca acc cta gat gcc gac aac gaa acg gaa     1728
Ser Asn Tyr Asp Tyr Asp Thr Thr Leu Asp Ala Asp Asn Glu Thr Glu
                565                 570                 575
```

-continued

```
cag cgt ttg gat tcc tct gct tat agc tgg gga gag gct gta caa aga        1776
Gln Arg Leu Asp Ser Ser Ala Tyr Ser Trp Gly Glu Ala Val Gln Arg
        580                 585                 590 cca agt gat gtc acc cct gta aaa ctc tct aaa atc aac taa                1818
Pro Ser Asp Val Thr Pro Val Lys Leu Ser Lys Ile Asn
        595                 600                 605
```

<210> SEQ ID NO 2
<211> LENGTH: 605
<212> TYPE: PRT
<213> ORGANISM: Babesia bovis

<400> SEQUENCE: 2

```
Met Gln Leu His Asn Lys Met Gln Ser Thr Ser Leu Lys Tyr Asn Tyr
1               5                   10                  15

Lys Arg Met Leu Cys Met Ala Leu Val Pro Val Ile Leu Ser Ser Phe
                20                  25                  30

Phe Ala Glu Asp Ala Leu Ala Ser Asn Ser Thr Leu Phe Ala Phe His
            35                  40                  45

Lys Glu Pro Asn Asn Arg Arg Leu Thr Lys Arg Ser Ser Arg Gly Gln
        50                  55                  60

Leu Leu Asn Ser Arg Arg Gly Ser Asp Ala Ser Glu Ser Ser Asp
65                  70                  75                  80

Arg Tyr Pro Gly Arg Ser Gly Gly Ser Lys Asn Ser Ser Gln Ser Pro
                85                  90                  95

Trp Ile Lys Tyr Met Gln Lys Phe Asp Ile Pro Arg Asn His Gly Ser
            100                 105                 110

Gly Ile Tyr Val Asp Leu Gly Gly Tyr Glu Ser Val Gly Ser Lys Ser
        115                 120                 125

Tyr Arg Met Pro Val Gly Lys Cys Pro Val Val Gly Lys Ile Ile Asp
130                 135                 140

Leu Gly Asn Gly Ala Asp Phe Leu Asp Pro Ile Ser Ser Asp Asp Pro
145                 150                 155                 160

Ser Tyr Arg Gly Leu Ala Phe Pro Glu Thr Ala Val Asp Ser Asn Ile
                165                 170                 175

Pro Thr Gln Pro Lys Thr Arg Gly Ser Ser Ala Ser Ala Ala Lys
            180                 185                 190

Leu Ser Pro Val Ser Ala Lys Asp Leu Arg Arg Trp Gly Tyr Glu Gly
        195                 200                 205

Asn Asp Val Ala Asn Cys Ser Glu Tyr Ala Ser Asn Leu Ile Pro Ala
    210                 215                 220

Ser Asp Arg Ser Thr Lys Tyr Arg Tyr Pro Phe Val Phe Asp Ser Asp
225                 230                 235                 240

Asn Gln Met Cys Tyr Ile Leu Tyr Ser Ala Ile Gln Tyr Asn Gln Gly
                245                 250                 255

Asn Arg Tyr Cys Asp Asn Asp Gly Ser Ser Glu Asp Gly Thr Ser Ser
            260                 265                 270

Leu Leu Cys Met Lys Pro Tyr Lys Ser Ala Glu Asp Ala His Leu Tyr
        275                 280                 285

Tyr Gly Ser Ala Lys Val Asp Pro Asp Trp Glu Glu Asn Cys Pro Met
    290                 295                 300

His Pro Val Arg Asp Ala Ile Phe Gly Lys Trp Ser Gly Gly Ser Cys
305                 310                 315                 320

Val Ala Ile Ala Pro Ala Phe Gln Glu Tyr Ala Asn Ser Thr Glu Asp
                325                 330                 335
```

-continued

```
Cys Ala Ala Ile Leu Phe Asp Asn Ser Ala Thr Asp Leu Asn Ile Glu
            340                 345                 350

Ala Val Asn Glu Asp Phe Asn Glu Leu Lys Glu Leu Thr Asp Gly Leu
            355                 360                 365

Lys Arg Leu Asn Met Ser Lys Val Ala Asn Ala Ile Phe Ser Pro Leu
            370                 375                 380

Ser Asn Val Ala Gly Thr Ser Arg Ile Ser Arg Gly Val Gly Met Asn
385                 390                 395                 400

Trp Ala Thr Tyr Asp Lys Asp Ser Gly Met Cys Ala Leu Ile Asn Glu
            405                 410                 415

Thr Pro Asn Cys Leu Ile Leu Asn Ala Gly Ser Ile Ala Leu Thr Ala
            420                 425                 430

Ile Gly Ser Pro Leu Glu Tyr Asp Ala Val Asn Tyr Pro Cys His Ile
            435                 440                 445

Asp Thr Asn Gly Tyr Val Glu Pro Arg Ala Lys Asn Thr Asn Lys Tyr
            450                 455                 460

Leu Asp Val Pro Phe Glu Val Thr Thr Ala Leu Ser Met Lys Thr Leu
465                 470                 475                 480

Lys Cys Asp Ala Tyr Val His Thr Lys Tyr Ser Asp Ser Cys Gly Thr
            485                 490                 495

Tyr Phe Leu Cys Ser Asp Val Lys Pro Asn Trp Phe Ile Arg Phe Leu
            500                 505                 510

His Met Ile Gly Leu Tyr Asn Thr Lys Arg Ile Val Ile Phe Val Cys
            515                 520                 525

Cys Thr Thr Thr Ala Ile Val Leu Thr Ile Trp Ile Trp Lys Arg Phe
            530                 535                 540

Ile Lys Ala Lys Lys Glu Pro Ala Pro Ser Phe Asp Lys Tyr Leu
545                 550                 555                 560

Ser Asn Tyr Asp Tyr Asp Thr Thr Leu Asp Ala Asp Asn Glu Thr Glu
            565                 570                 575

Gln Arg Leu Asp Ser Ser Ala Tyr Ser Trp Gly Glu Ala Val Gln Arg
            580                 585                 590

Pro Ser Asp Val Thr Pro Val Lys Leu Ser Lys Ile Asn
            595                 600                 605

<210> SEQ ID NO 3
<211> LENGTH: 2349
<212> TYPE: DNA
<213> ORGANISM: Theileria annulata
<220> FEATURE:
<221> NAME/KEY: CDS
<222> LOCATION: (1)..(2349)

<400> SEQUENCE: 3 atg aaa aaa ata gga ctt aaa att agg gca caa aag gat aaa tta aat      48
Met Lys Lys Ile Gly Leu Lys Ile Arg Ala Gln Lys Asp Lys Leu Asn
1               5                   10                  15 cct gtg tta gga agc aac tct gac cct tcg gaa gag tat gat tca ttc      96
Pro Val Leu Gly Ser Asn Ser Asp Pro Ser Glu Glu Tyr Asp Ser Phe
            20                  25                  30 cag caa aat gtt ttc act cat caa cca acc caa cta cac aaa tct cat     144
Gln Gln Asn Val Phe Thr His Gln Pro Thr Gln Leu His Lys Ser His
        35                  40                  45 cac tac att aca cac cag aaa aaa acc agc caa cac atc gac gat tta     192
His Tyr Ile Thr His Gln Lys Lys Thr Ser Gln His Ile Asp Asp Leu
    50                  55                  60
```

```
aat ttt tat aat gga aaa ttt aat caa aag agc aga att ggt cca ggg      240
Asn Phe Tyr Asn Gly Lys Phe Asn Gln Lys Ser Arg Ile Gly Pro Gly
 65              70                  75                  80 aag gta gta aat aac agt agg aat ctg gta gaa ggt gaa aca cta tct      288
Lys Val Val Asn Asn Ser Arg Asn Leu Val Glu Gly Glu Thr Leu Ser
                 85                  90                  95 aag gat gac aat aaa aca aaa tct aaa ata aag tca aaa aca gca tca      336
Lys Asp Asp Asn Lys Thr Lys Ser Lys Ile Lys Ser Lys Thr Ala Ser
             100                 105                 110 att tta cct aga ctt tta aaa tct tta tca ttt tta gct gtt tta ggg      384
Ile Leu Pro Arg Leu Leu Lys Ser Leu Ser Phe Leu Ala Val Leu Gly
         115                 120                 125 tca att aat tca ttt tca tta gca tta gag gaa cct ttt act caa cac      432
Ser Ile Asn Ser Phe Ser Leu Ala Leu Glu Glu Pro Phe Thr Gln His
    130                 135                 140 act tct aac cga acg ccc ttt gaa gta tca tta att caa agc aac agc      480
Thr Ser Asn Arg Thr Pro Phe Glu Val Ser Leu Ile Gln Ser Asn Ser
145                 150                 155                 160 agt tta tcg cct att cat aat tct tca act caa aat tca agt cat cac      528
Ser Leu Ser Pro Ile His Asn Ser Ser Thr Gln Asn Ser Ser His His
                 165                 170                 175 aac ggt ttt agt ggt agt acc gtt aat aat acc tca tta ata gag aca      576
Asn Gly Phe Ser Gly Ser Thr Val Asn Asn Thr Ser Leu Ile Glu Thr
             180                 185                 190 agg aat aac gta tta aac aga aca cta ggt aga ttc gga tca ttt ttg      624
Arg Asn Asn Val Leu Asn Arg Thr Leu Gly Arg Phe Gly Ser Phe Leu
         195                 200                 205 caa tca gga ttg ata agc agt aga gca gac aaa aag aag cgg tct ggt      672
Gln Ser Gly Leu Ile Ser Ser Arg Ala Asp Lys Lys Lys Arg Ser Gly
    210                 215                 220 atg aat aga aga ggc cct aag ggg aag aaa ggg aag gga gga gaa gac      720
Met Asn Arg Arg Gly Pro Lys Gly Lys Lys Gly Lys Gly Gly Glu Asp
225                 230                 235                 240 gaa gaa aag agg aac aag tgg acc gat ttc atg gca aag ttt gat atc      768
Glu Glu Lys Arg Asn Lys Trp Thr Asp Phe Met Ala Lys Phe Asp Ile
                 245                 250                 255 gct aag gtc cac ggt tca ggg gtt tac gta gat ttg ggt gaa tct gcc      816
Ala Lys Val His Gly Ser Gly Val Tyr Val Asp Leu Gly Glu Ser Ala
             260                 265                 270 acc gtt ggc agt tat gac tac agg atg cct ata gga aaa tgt cca gtt      864
Thr Val Gly Ser Tyr Asp Tyr Arg Met Pro Ile Gly Lys Cys Pro Val
         275                 280                 285 gta ggt aag gca atc ata ctc gag aat gga gct gat ttt ttg agc agc      912
Val Gly Lys Ala Ile Ile Leu Glu Asn Gly Ala Asp Phe Leu Ser Ser
    290                 295                 300 ata acc cat cat gac ccc aag gag aga ggg ctg ggg ttc cct gct aca      960
Ile Thr His His Asp Pro Lys Glu Arg Gly Leu Gly Phe Pro Ala Thr
305                 310                 315                 320 aaa gtt gcc tca aat tca tca aaa ctg gac atg gag aac cag ctc tta     1008
Lys Val Ala Ser Asn Ser Ser Lys Leu Asp Met Glu Asn Gln Leu Leu
                 325                 330                 335 tca cca att agt gct cag gtc cta agg agc tgg aat tat aaa cac gaa     1056
Ser Pro Ile Ser Ala Gln Val Leu Arg Ser Trp Asn Tyr Lys His Glu
             340                 345                 350 tca gat tta agt aat tgt gct gag tat tcg aga aac att gtt ccg ggc     1104
Ser Asp Leu Ser Asn Cys Ala Glu Tyr Ser Arg Asn Ile Val Pro Gly
         355                 360                 365 agt aat cgt aat tca aag tat cgt tac ccg ttt gta tat gat gag tct     1152
Ser Asn Arg Asn Ser Lys Tyr Arg Tyr Pro Phe Val Tyr Asp Glu Ser
    370                 375                 380
```

| | | |
|---|---|---|
| gag aag ctt tgt tat att tta tat agt ccc atg caa tat aat cag ggc<br>Glu Lys Leu Cys Tyr Ile Leu Tyr Ser Pro Met Gln Tyr Asn Gln Gly<br>385                     390              395                400 | | 1200 |
| gta aag tac tgt gac caa gac tct ccg gac gaa gga act agc agt tta<br>Val Lys Tyr Cys Asp Gln Asp Ser Pro Asp Glu Gly Thr Ser Ser Leu<br>                      405                410                415 | | 1248 |
| gct tgt atg tac ccg gat aag agc aag gag gat tca cac cta ttt tac<br>Ala Cys Met Tyr Pro Asp Lys Ser Lys Glu Asp Ser His Leu Phe Tyr<br>420                     425              430 | | 1296 |
| gga acc agc ggt ctt cac atg gac tgg cct gta gtt tgc cca gtt tac<br>Gly Thr Ser Gly Leu His Met Asp Trp Pro Val Val Cys Pro Val Tyr<br>                 435                440              445 | | 1344 |
| cct att aga gat tcg att ttt gga tcc tac gac gac caa aag gac gaa<br>Pro Ile Arg Asp Ser Ile Phe Gly Ser Tyr Asp Asp Gln Lys Asp Glu<br>450                     455              460 | | 1392 |
| tgt gtt cca att gag ccg ata ttt gag gag gag gct gaa gat tat gag<br>Cys Val Pro Ile Glu Pro Ile Phe Glu Glu Glu Ala Glu Asp Tyr Glu<br>465                     470              475                480 | | 1440 |
| gca tgt gcc aag ata att ttc gag tat tct cca agt gat gtt gat att<br>Ala Cys Ala Lys Ile Ile Phe Glu Tyr Ser Pro Ser Asp Val Asp Ile<br>                 485                490              495 | | 1488 |
| agc aca aat aac cag aag ctt tca gac gtc gac ctt tac aag gag gcg<br>Ser Thr Asn Asn Gln Lys Leu Ser Asp Val Asp Leu Tyr Lys Glu Ala<br>                 500                505              510 | | 1536 |
| atg aat aat gga aag ctg agc act gct ctt tca att atg ttt gct cct<br>Met Asn Asn Gly Lys Leu Ser Thr Ala Leu Ser Ile Met Phe Ala Pro<br>515                     520              525 | | 1584 |
| agg tac tct gag gat cgt ccg atc tat act aaa ggt gtc ggt ata aac<br>Arg Tyr Ser Glu Asp Arg Pro Ile Tyr Thr Lys Gly Val Gly Ile Asn<br>530                     535              540 | | 1632 |
| tgg gct aca tac tcc gtc gag gaa aag aaa tgt aac att ctc gac gtt<br>Trp Ala Thr Tyr Ser Val Glu Glu Lys Lys Cys Asn Ile Leu Asp Val<br>545                     550              555                560 | | 1680 |
| gtt ccc agc tgt ctt att ata agt aac ggc cac tat gcc ctt aca agt<br>Val Pro Ser Cys Leu Ile Ile Ser Asn Gly His Tyr Ala Leu Thr Ser<br>                 565                570              575 | | 1728 |
| ctc agc tca ccc aat gaa gag gat gct ata aat tac ccc tgc gat atc<br>Leu Ser Ser Pro Asn Glu Glu Asp Ala Ile Asn Tyr Pro Cys Asp Ile<br>                 580                585              590 | | 1776 |
| gtt cag ggc aag ggg ttt ttg aag aac cca aac ggt gga aaa aag aat<br>Val Gln Gly Lys Gly Phe Leu Lys Asn Pro Asn Gly Gly Lys Lys Asn<br>595                     600              605 | | 1824 |
| gct cag gaa ccg ccc aag gaa cct gaa cct gaa gaa cct aag aag gag<br>Ala Gln Glu Pro Pro Lys Glu Pro Glu Pro Glu Glu Pro Lys Lys Glu<br>610                     615              620 | | 1872 |
| ggt gct gaa aac aaa ccc aaa gag aaa ggt aaa tct gag aaa aag aat<br>Gly Ala Glu Asn Lys Pro Lys Glu Lys Gly Lys Ser Glu Lys Lys Asn<br>625                     630              635                640 | | 1920 |
| gaa aaa tct atg cct tca gga cca ttc acg cca tac act agc ttg aag<br>Glu Lys Ser Met Pro Ser Gly Pro Phe Thr Pro Tyr Thr Ser Leu Lys<br>                 645                650              655 | | 1968 |
| aag gag ggt ttc gag tgc agt aaa tac act gtt gag cgg gtg aac aaa<br>Lys Glu Gly Phe Glu Cys Ser Lys Tyr Thr Val Glu Arg Val Asn Lys<br>660                     665              670 | | 2016 |
| agc tgc ggc gtt tac tat gaa tgc tca gaa acg cct gta tta ttt acc<br>Ser Cys Gly Val Tyr Tyr Glu Cys Ser Glu Thr Pro Val Leu Phe Thr<br>675                     680              685 | | 2064 |
| aag aag aat agg att tat cta tac atc ata ttg gca gta tcg ctt gta<br>Lys Lys Asn Arg Ile Tyr Leu Tyr Ile Ile Leu Ala Val Ser Leu Val | | 2112 |

-continued

```
              690                 695                 700
gta ctg gcc gtc tta gcc tac ttt gga tac agg tac tac agt aag aat       2160
Val Leu Ala Val Leu Ala Tyr Phe Gly Tyr Arg Tyr Tyr Ser Lys Asn
705                 710                 715                 720 cac ttg aaa aaa cac aat tcc cag ata tat gaa gat gat aac gtg aac       2208
His Leu Lys Lys His Asn Ser Gln Ile Tyr Glu Asp Asp Asn Val Asn
                725                 730                 735 aac tac tac aat gag gac ttt gat gac gaa caa gat cgg gat gaa tac       2256
Asn Tyr Tyr Asn Glu Asp Phe Asp Asp Glu Gln Asp Arg Asp Glu Tyr
            740                 745                 750 gct tcg aat gtt aga ggt gat caa atc tgg agc aga cac act cca gac       2304
Ala Ser Asn Val Arg Gly Asp Gln Ile Trp Ser Arg His Thr Pro Asp
        755                 760                 765 aga tct gaa gtt act cca gtc aga atc tct agg tta aac cat taa           2349
Arg Ser Glu Val Thr Pro Val Arg Ile Ser Arg Leu Asn His
    770                 775                 780
```

<210> SEQ ID NO 4
<211> LENGTH: 782
<212> TYPE: PRT
<213> ORGANISM: Theileria annulata

<400> SEQUENCE: 4

```
Met Lys Lys Ile Gly Leu Lys Ile Arg Ala Gln Lys Asp Lys Leu Asn
1               5                   10                  15

Pro Val Leu Gly Ser Asn Ser Asp Pro Ser Glu Glu Tyr Asp Ser Phe
            20                  25                  30

Gln Gln Asn Val Phe Thr His Gln Pro Thr Gln Leu His Lys Ser His
        35                  40                  45

His Tyr Ile Thr His Gln Lys Lys Thr Ser Gln His Ile Asp Asp Leu
    50                  55                  60

Asn Phe Tyr Asn Gly Lys Phe Asn Gln Lys Ser Arg Ile Gly Pro Gly
65                  70                  75                  80

Lys Val Val Asn Asn Ser Arg Asn Leu Val Glu Gly Glu Thr Leu Ser
                85                  90                  95

Lys Asp Asp Asn Lys Thr Lys Ser Lys Ile Lys Ser Lys Thr Ala Ser
            100                 105                 110

Ile Leu Pro Arg Leu Leu Lys Ser Leu Ser Phe Leu Ala Val Leu Gly
        115                 120                 125

Ser Ile Asn Ser Phe Ser Leu Ala Leu Glu Glu Pro Phe Thr Gln His
    130                 135                 140

Thr Ser Asn Arg Thr Pro Phe Glu Val Ser Leu Ile Gln Ser Asn Ser
145                 150                 155                 160

Ser Leu Ser Pro Ile His Asn Ser Ser Thr Gln Asn Ser Ser His His
                165                 170                 175

Asn Gly Phe Ser Gly Ser Thr Val Asn Asn Thr Ser Leu Ile Glu Thr
            180                 185                 190

Arg Asn Asn Val Leu Asn Arg Thr Leu Gly Arg Phe Gly Ser Phe Leu
        195                 200                 205

Gln Ser Gly Leu Ile Ser Ser Arg Ala Asp Lys Lys Arg Ser Gly
    210                 215                 220

Met Asn Arg Arg Gly Pro Lys Gly Lys Gly Lys Gly Gly Glu Asp
225                 230                 235                 240

Glu Glu Lys Arg Asn Lys Trp Thr Asp Phe Met Ala Lys Phe Asp Ile
                245                 250                 255

Ala Lys Val His Gly Ser Gly Val Tyr Val Asp Leu Gly Glu Ser Ala
```

-continued

```
                260                 265                 270
Thr Val Gly Ser Tyr Asp Tyr Arg Met Pro Ile Gly Lys Cys Pro Val
            275                 280                 285
Val Gly Lys Ala Ile Ile Leu Glu Asn Gly Ala Asp Phe Leu Ser Ser
        290                 295                 300
Ile Thr His His Asp Pro Lys Glu Arg Gly Leu Gly Phe Pro Ala Thr
305                 310                 315                 320
Lys Val Ala Ser Asn Ser Ser Lys Leu Asp Met Glu Asn Gln Leu Leu
                325                 330                 335
Ser Pro Ile Ser Ala Gln Val Leu Arg Ser Trp Asn Tyr Lys His Glu
            340                 345                 350
Ser Asp Leu Ser Asn Cys Ala Glu Tyr Ser Arg Asn Ile Val Pro Gly
        355                 360                 365
Ser Asn Arg Asn Ser Lys Tyr Arg Tyr Pro Phe Val Tyr Asp Glu Ser
    370                 375                 380
Glu Lys Leu Cys Tyr Ile Leu Tyr Ser Pro Met Gln Tyr Asn Gln Gly
385                 390                 395                 400
Val Lys Tyr Cys Asp Gln Asp Ser Pro Asp Glu Gly Thr Ser Ser Leu
                405                 410                 415
Ala Cys Met Tyr Pro Asp Lys Ser Lys Glu Asp Ser His Leu Phe Tyr
            420                 425                 430
Gly Thr Ser Gly Leu His Met Asp Trp Pro Val Val Cys Pro Val Tyr
        435                 440                 445
Pro Ile Arg Asp Ser Ile Phe Gly Ser Tyr Asp Gln Lys Asp Glu
    450                 455                 460
Cys Val Pro Ile Glu Pro Ile Phe Glu Glu Ala Glu Asp Tyr Glu
465                 470                 475                 480
Ala Cys Ala Lys Ile Ile Phe Glu Tyr Ser Pro Ser Asp Val Asp Ile
            485                 490                 495
Ser Thr Asn Asn Gln Lys Leu Ser Asp Val Asp Leu Tyr Lys Glu Ala
        500                 505                 510
Met Asn Asn Gly Lys Leu Ser Thr Ala Leu Ser Ile Met Phe Ala Pro
    515                 520                 525
Arg Tyr Ser Glu Asp Arg Pro Ile Tyr Thr Lys Gly Val Gly Ile Asn
    530                 535                 540
Trp Ala Thr Tyr Ser Val Glu Glu Lys Lys Cys Asn Ile Leu Asp Val
545                 550                 555                 560
Val Pro Ser Cys Leu Ile Ile Ser Asn Gly His Tyr Ala Leu Thr Ser
            565                 570                 575
Leu Ser Ser Pro Asn Glu Glu Asp Ala Ile Asn Tyr Pro Cys Asp Ile
        580                 585                 590
Val Gln Gly Lys Gly Phe Leu Lys Asn Pro Asn Gly Lys Lys Asn
    595                 600                 605
Ala Gln Glu Pro Pro Lys Glu Pro Glu Pro Glu Pro Lys Lys Glu
    610                 615                 620
Gly Ala Glu Asn Lys Pro Lys Glu Lys Gly Lys Ser Glu Lys Asn
625                 630                 635                 640
Glu Lys Ser Met Pro Ser Gly Pro Phe Thr Pro Tyr Thr Ser Leu Lys
                645                 650                 655
Lys Glu Gly Phe Glu Cys Ser Lys Tyr Thr Val Glu Arg Val Asn Lys
            660                 665                 670
Ser Cys Gly Val Tyr Tyr Glu Cys Ser Glu Thr Pro Val Leu Phe Thr
        675                 680                 685
```

```
Lys Lys Asn Arg Ile Tyr Leu Tyr Ile Ile Leu Ala Val Ser Leu Val
    690             695                 700

Val Leu Ala Val Leu Ala Tyr Phe Gly Tyr Arg Tyr Tyr Ser Lys Asn
705             710                 715                 720

His Leu Lys Lys His Asn Ser Gln Ile Tyr Glu Asp Asp Asn Val Asn
            725                 730                 735

Asn Tyr Tyr Asn Glu Asp Phe Asp Asp Glu Gln Asp Arg Asp Glu Tyr
                740                 745                 750

Ala Ser Asn Val Arg Gly Asp Gln Ile Trp Ser Arg His Thr Pro Asp
        755                 760                 765

Arg Ser Glu Val Thr Pro Val Arg Ile Ser Arg Leu Asn His
    770                 775                 780

<210> SEQ ID NO 5
<211> LENGTH: 1968
<212> TYPE: DNA
<213> ORGANISM: Babesia bovis
<220> FEATURE:
<221> NAME/KEY: CDS
<222> LOCATION: (1)..(1968)

<400> SEQUENCE: 5 atg atc ggt tac atc aag att ctg gcc tct gtg ccc ctg tta agt tta      48
Met Ile Gly Tyr Ile Lys Ile Leu Ala Ser Val Pro Leu Leu Ser Leu
1               5                  10                  15 gcc ttt tta gct aca acg ggg ata cat gct ttt gcg gac aaa ggt att     96
Ala Phe Leu Ala Thr Thr Gly Ile His Ala Phe Ala Asp Lys Gly Ile
            20                  25                  30 ggt tca cca aag ggg aaa caa tgc aag aag caa ctt gac ttt tcg att    144
Gly Ser Pro Lys Gly Lys Gln Cys Lys Lys Gln Leu Asp Phe Ser Ile
        35                  40                  45 gtg gta gat gaa tct gct agt ata tcg gat gat caa tgg gag ggt cag    192
Val Val Asp Glu Ser Ala Ser Ile Ser Asp Asp Gln Trp Glu Gly Gln
    50                  55                  60 atg att cca ttt ttg agg aat ttg att cat acc gtt gac ctt gac aac    240
Met Ile Pro Phe Leu Arg Asn Leu Ile His Thr Val Asp Leu Asp Asn
65                  70                  75                  80 act gac ata cgt ctt tcg ctt acc act tac tca act cca act cgc cag    288
Thr Asp Ile Arg Leu Ser Leu Thr Thr Tyr Ser Thr Pro Thr Arg Gln
                85                  90                  95 ata ttt acg ttt ttg gat gct gct gca agc agt acc agg ctc gca ctc    336
Ile Phe Thr Phe Leu Asp Ala Ala Ala Ser Ser Thr Arg Leu Ala Leu
            100                 105                 110 acg aaa ctt gat tgg atg aac ggt acc aaa gct agg tat ggt atg acc    384
Thr Lys Leu Asp Trp Met Asn Gly Thr Lys Ala Arg Tyr Gly Met Thr
        115                 120                 125 tac act ggc agg gct ctg aac tac gtt cgt aag gct ata cta cca tat    432
Tyr Thr Gly Arg Ala Leu Asn Tyr Val Arg Lys Ala Ile Leu Pro Tyr
    130                 135                 140 ggt cgc aag aat gta ccc aag gca ctg tta ctg atc act gat gga gta    480
Gly Arg Lys Asn Val Pro Lys Ala Leu Leu Leu Ile Thr Asp Gly Val
145                 150                 155                 160 tct tcg gat gga agt tac act gca cag gtt gcg gct atg ctt cgt gat    528
Ser Ser Asp Gly Ser Tyr Thr Ala Gln Val Ala Ala Met Leu Arg Asp
                165                 170                 175 gaa ggt gta aat gta atg gtt att ggt gtc ggt gat gta aat gtt gct    576
Glu Gly Val Asn Val Met Val Ile Gly Val Gly Asp Val Asn Val Ala
            180                 185                 190 gaa tgc cgt ggc ata gta gga tgt gat gga ata atg gat tgt cct atg    624
```

```
                Glu Cys Arg Gly Ile Val Gly Cys Asp Gly Ile Met Asp Cys Pro Met
                            195                 200                 205 ttc aag cag acc aac tgg aag gat atc atg ggc ctc ttt aac agt tta           672
Phe Lys Gln Thr Asn Trp Lys Asp Ile Met Gly Leu Phe Asn Ser Leu
        210                 215                 220 atg aag gag gta tgt gat att tta cct cag gac gct gtt tgt gag cct           720
Met Lys Glu Val Cys Asp Ile Leu Pro Gln Asp Ala Val Cys Glu Pro
225                 230                 235                 240 gta tgg gca gaa tgg tca tct tgt aac ggg gaa tgt ggc gtt cct ggt           768
Val Trp Ala Glu Trp Ser Ser Cys Asn Gly Glu Cys Gly Val Pro Gly
                245                 250                 255 aaa cga act cgt gct ctt ttg gac ctc cga atg att gaa aag ccc gta           816
Lys Arg Thr Arg Ala Leu Leu Asp Leu Arg Met Ile Glu Lys Pro Val
        260                 265                 270 aat ggc tcg aat gga caa ccg ggt aaa tca tgt gag gat cag aag atg           864
Asn Gly Ser Asn Gly Gln Pro Gly Lys Ser Cys Glu Asp Gln Lys Met
275                 280                 285 aac ttc tta ccc caa tca gag aca tgc acc ata gaa tgc aat cat gag           912
Asn Phe Leu Pro Gln Ser Glu Thr Cys Thr Ile Glu Cys Asn His Glu
        290                 295                 300 cct gtg cca agc tcg ccg gaa cct gta tca gat gat atg gat cac cca           960
Pro Val Pro Ser Ser Pro Glu Pro Val Ser Asp Asp Met Asp His Pro
305                 310                 315                 320 gaa cca act cct gtt aca ccg gaa ggt gac atg gat aaa tct cat tcc          1008
Glu Pro Thr Pro Val Thr Pro Glu Gly Asp Met Asp Lys Ser His Ser
                325                 330                 335 cat tcg agc att cca tcc acc cct gat atg cca tca agt cac agt gat          1056
His Ser Ser Ile Pro Ser Thr Pro Asp Met Pro Ser Ser His Ser Asp
        340                 345                 350 atg tca tca agc cct act gat atg tca tca agc cct act gac atg tca          1104
Met Ser Ser Ser Pro Thr Asp Met Ser Ser Ser Pro Thr Asp Met Ser
355                 360                 365 tca agc cct act gac atg tca tca agt cac agt gac atg cca tca act          1152
Ser Ser Pro Thr Asp Met Ser Ser His Ser Asp Met Pro Ser Thr
        370                 375                 380 cct act ggc atg tca tca agt cac agt gat atg cca tca agt cac agt          1200
Pro Thr Gly Met Ser Ser Ser His Ser Asp Met Pro Ser Ser His Ser
385                 390                 395                 400 gat atg cca tca agc cac agt gat atg tca tca agc cct act gac atg          1248
Asp Met Pro Ser Ser His Ser Asp Met Ser Ser Ser Pro Thr Asp Met
                405                 410                 415 tca tca agt cac gct gat act cgt gta gga aat acc gat gaa gaa cat          1296
Ser Ser Ser His Ala Asp Thr Arg Val Gly Asn Thr Asp Glu Glu His
        420                 425                 430 aac cac agg aaa gat atg gat gtc aag ttc ccc gaa aat atg gat gat          1344
Asn His Arg Lys Asp Met Asp Val Lys Phe Pro Glu Asn Met Asp Asp
435                 440                 445 atc cca gtc gag gat aat cct ata ccc aca gat cct aga cat ggc gtc          1392
Ile Pro Val Glu Asp Asn Pro Ile Pro Thr Asp Pro Arg His Gly Val
                450                 455                 460 gaa cca tcg cct tct gat gtg atc cct gag gat gac caa ctt cgt agg          1440
Glu Pro Ser Pro Ser Asp Val Ile Pro Glu Asp Asp Gln Leu Arg Arg
465                 470                 475                 480 acg ctt gaa atg cag cgc gaa gag gac cta aag aag gaa ttg atg ctc          1488
Thr Leu Glu Met Gln Arg Glu Glu Asp Leu Lys Lys Glu Leu Met Leu
        485                 490                 495 caa cat gaa ctg aag ctt cag gaa gaa aag gaa agg gca gct att tta          1536
Gln His Glu Leu Lys Leu Gln Glu Glu Lys Glu Arg Ala Ala Ile Leu
500                 505                 510
```

```
gag aat aac act cct tat gga tcc gcc act tcc gtg tcg caa gac ggt      1584
Glu Asn Asn Thr Pro Tyr Gly Ser Ala Thr Ser Val Ser Gln Asp Gly
            515                 520                 525 gaa tct cca act ggc gta ccc caa agt agc gag acc gat gca ata cgt      1632
Glu Ser Pro Thr Gly Val Pro Gln Ser Ser Glu Thr Asp Ala Ile Arg
        530                 535                 540 cac gag gtg tat gac gat cac ccc gag gaa tct gaa aac acc ggg att      1680
His Glu Val Tyr Asp Asp His Pro Glu Glu Ser Glu Asn Thr Gly Ile
545                 550                 555                 560 aat gct gat gtg acc gaa tct gag gac tat gag ggt gaa aaa caa aag      1728
Asn Ala Asp Val Thr Glu Ser Glu Asp Tyr Glu Gly Glu Lys Gln Lys
                565                 570                 575 gac gaa tca aat gaa cgt tcg acc agc aac act act aag att gcc ggc      1776
Asp Glu Ser Asn Glu Arg Ser Thr Ser Asn Thr Thr Lys Ile Ala Gly
            580                 585                 590 ggt gct cta cta ggt ctt ctt ctc ctt ggt gcc ggt ggt gga tac gct      1824
Gly Ala Leu Leu Gly Leu Leu Leu Leu Gly Ala Gly Gly Gly Tyr Ala
        595                 600                 605 atg tac aaa aag aac aag aca cct act gtt gag aca ggt tca ggt gat      1872
Met Tyr Lys Lys Asn Lys Thr Pro Thr Val Glu Thr Gly Ser Gly Asp
    610                 615                 620 tac act ggg gcc gac gag agt tca gaa ccc atg aag gag ggt gac aca      1920
Tyr Thr Gly Ala Asp Glu Ser Ser Glu Pro Met Lys Glu Gly Asp Thr
625                 630                 635                 640 tac acc gtc act gag ttt gac aac aac att tgg ggc gag gca gcg taa      1968
Tyr Thr Val Thr Glu Phe Asp Asn Asn Ile Trp Gly Glu Ala Ala
                645                 650                 655

<210> SEQ ID NO 6
<211> LENGTH: 655
<212> TYPE: PRT
<213> ORGANISM: Babesia bovis

<400> SEQUENCE: 6

Met Ile Gly Tyr Ile Lys Ile Leu Ala Ser Val Pro Leu Leu Ser Leu
1               5                   10                  15

Ala Phe Leu Ala Thr Thr Gly Ile His Ala Phe Ala Asp Lys Gly Ile
            20                  25                  30

Gly Ser Pro Lys Gly Lys Gln Cys Lys Lys Gln Leu Asp Phe Ser Ile
        35                  40                  45

Val Val Asp Glu Ser Ala Ser Ile Ser Asp Asp Gln Trp Glu Gly Gln
    50                  55                  60

Met Ile Pro Phe Leu Arg Asn Leu Ile His Thr Val Asp Leu Asp Asn
65                  70                  75                  80

Thr Asp Ile Arg Leu Ser Leu Thr Thr Tyr Ser Thr Pro Thr Arg Gln
                85                  90                  95

Ile Phe Thr Phe Leu Asp Ala Ala Ser Ser Thr Arg Leu Ala Leu
            100                 105                 110

Thr Lys Leu Asp Trp Met Asn Gly Thr Lys Ala Arg Tyr Gly Met Thr
        115                 120                 125

Tyr Thr Gly Arg Ala Leu Asn Tyr Val Arg Lys Ala Ile Leu Pro Tyr
    130                 135                 140

Gly Arg Lys Asn Val Pro Lys Ala Leu Leu Leu Ile Thr Asp Gly Val
145                 150                 155                 160

Ser Ser Asp Gly Ser Tyr Thr Ala Gln Val Ala Ala Met Leu Arg Asp
                165                 170                 175

Glu Gly Val Asn Val Met Val Ile Gly Val Gly Asp Val Asn Val Ala
            180                 185                 190
```

-continued

```
Glu Cys Arg Gly Ile Val Gly Cys Asp Gly Ile Met Asp Cys Pro Met
        195                 200                 205
Phe Lys Gln Thr Asn Trp Lys Asp Ile Met Gly Leu Phe Asn Ser Leu
    210                 215                 220
Met Lys Glu Val Cys Asp Ile Leu Pro Gln Asp Ala Val Cys Glu Pro
225                 230                 235                 240
Val Trp Ala Glu Trp Ser Ser Cys Asn Gly Cys Gly Val Pro Gly
                245                 250                 255
Lys Arg Thr Arg Ala Leu Leu Asp Leu Arg Met Ile Glu Lys Pro Val
            260                 265                 270
Asn Gly Ser Asn Gly Gln Pro Gly Lys Ser Cys Glu Asp Gln Lys Met
        275                 280                 285
Asn Phe Leu Pro Gln Ser Glu Thr Cys Thr Ile Glu Cys Asn His Glu
    290                 295                 300
Pro Val Pro Ser Ser Pro Glu Pro Val Ser Asp Asp Met Asp His Pro
305                 310                 315                 320
Glu Pro Thr Pro Val Thr Pro Glu Gly Asp Met Asp Lys Ser His Ser
                325                 330                 335
His Ser Ser Ile Pro Ser Thr Pro Asp Met Pro Ser Ser His Ser Asp
            340                 345                 350
Met Ser Ser Ser Pro Thr Asp Met Ser Ser Pro Thr Asp Met Ser
        355                 360                 365
Ser Ser Pro Thr Asp Met Ser Ser Ser His Ser Asp Met Pro Ser Thr
    370                 375                 380
Pro Thr Gly Met Ser Ser Ser His Ser Asp Met Pro Ser Ser His Ser
385                 390                 395                 400
Asp Met Pro Ser Ser His Ser Asp Met Ser Ser Pro Thr Asp Met
                405                 410                 415
Ser Ser Ser His Ala Asp Thr Arg Val Gly Asn Thr Asp Glu Glu His
            420                 425                 430
Asn His Arg Lys Asp Met Asp Val Lys Phe Pro Glu Asn Met Asp Asp
        435                 440                 445
Ile Pro Val Glu Asp Asn Pro Ile Pro Thr Asp Pro Arg His Gly Val
    450                 455                 460
Glu Pro Ser Pro Ser Asp Val Ile Pro Glu Asp Asp Gln Leu Arg Arg
465                 470                 475                 480
Thr Leu Glu Met Gln Arg Glu Glu Asp Leu Lys Lys Glu Leu Met Leu
                485                 490                 495
Gln His Glu Leu Lys Leu Gln Glu Glu Lys Glu Arg Ala Ala Ile Leu
            500                 505                 510
Glu Asn Asn Thr Pro Tyr Gly Ser Ala Thr Ser Val Ser Gln Asp Gly
        515                 520                 525
Glu Ser Pro Thr Gly Val Pro Gln Ser Ser Glu Thr Asp Ala Ile Arg
    530                 535                 540
His Glu Val Tyr Asp Asp His Pro Glu Glu Ser Glu Asn Thr Gly Ile
545                 550                 555                 560
Asn Ala Asp Val Thr Glu Ser Glu Asp Tyr Glu Gly Glu Lys Gln Lys
                565                 570                 575
Asp Glu Ser Asn Glu Arg Ser Thr Ser Asn Thr Thr Lys Ile Ala Gly
            580                 585                 590
Gly Ala Leu Leu Gly Leu Leu Leu Gly Ala Gly Gly Gly Tyr Ala
        595                 600                 605
```

| Met | Tyr | Lys | Lys | Asn | Lys | Thr | Pro | Thr | Val | Glu | Thr | Gly | Ser | Gly | Asp |
| --- | --- | --- | --- | --- | --- | --- | --- | --- | --- | --- | --- | --- | --- | --- | --- |
| | 610 | | | | 615 | | | | 620 | | | | | | |

| Tyr | Thr | Gly | Ala | Asp | Glu | Ser | Ser | Glu | Pro | Met | Lys | Glu | Gly | Asp | Thr |
| --- | --- | --- | --- | --- | --- | --- | --- | --- | --- | --- | --- | --- | --- | --- | --- |
| 625 | | | | | 630 | | | | | 635 | | | | | 640 |

| Tyr | Thr | Val | Thr | Glu | Phe | Asp | Asn | Asn | Ile | Trp | Gly | Glu | Ala | Ala |
| --- | --- | --- | --- | --- | --- | --- | --- | --- | --- | --- | --- | --- | --- | --- |
| | | | 645 | | | | | 650 | | | | | 655 | |

```
<210> SEQ ID NO 7
<211> LENGTH: 1047
<212> TYPE: DNA
<213> ORGANISM: Theileria annulata
<220> FEATURE:
<221> NAME/KEY: CDS
<222> LOCATION: (1)..(1047)

<400> SEQUENCE: 7
```

| gat | aag | ggg | cta | tat | cct | gac | ggt | ata | aag | aaa | ccg | agc | tcc | tac | tgc | 48 |
| --- | --- | --- | --- | --- | --- | --- | --- | --- | --- | --- | --- | --- | --- | --- | --- | --- |
| Asp | Lys | Gly | Leu | Tyr | Pro | Asp | Gly | Ile | Lys | Lys | Pro | Ser | Ser | Tyr | Cys | |
| 1 | | | | 5 | | | | | 10 | | | | | 15 | | |

| cac | agg | gaa | ttg | gac | tta | aca | ata | tta | gtc | gat | gaa | tcc | tcg | agt | atc | 96 |
| --- | --- | --- | --- | --- | --- | --- | --- | --- | --- | --- | --- | --- | --- | --- | --- | --- |
| His | Arg | Glu | Leu | Asp | Leu | Thr | Ile | Leu | Val | Asp | Glu | Ser | Ser | Ser | Ile | |
| | | | 20 | | | | 25 | | | | | 30 | | | | |

| tat | att | gaa | gag | tgg | aac | aaa | ctc | att | cca | ttt | ctt | aaa | tca | ctg | gtg | 144 |
| --- | --- | --- | --- | --- | --- | --- | --- | --- | --- | --- | --- | --- | --- | --- | --- | --- |
| Tyr | Ile | Glu | Glu | Trp | Asn | Lys | Leu | Ile | Pro | Phe | Leu | Lys | Ser | Leu | Val | |
| | | 35 | | | | | 40 | | | | | 45 | | | | |

| aga | tca | ata | aat | ata | agt | cca | aat | tat | gtg | cac | ttg | tca | atg | gtc | acc | 192 |
| --- | --- | --- | --- | --- | --- | --- | --- | --- | --- | --- | --- | --- | --- | --- | --- | --- |
| Arg | Ser | Ile | Asn | Ile | Ser | Pro | Asn | Tyr | Val | His | Leu | Ser | Met | Val | Thr | |
| 50 | | | | | 55 | | | | | 60 | | | | | | |

| ttt | tcc | act | tca | att | cgg | tgg | tta | ata | tca | ttt | ctc | gac | cca | gcc | tct | 240 |
| --- | --- | --- | --- | --- | --- | --- | --- | --- | --- | --- | --- | --- | --- | --- | --- | --- |
| Phe | Ser | Thr | Ser | Ile | Arg | Trp | Leu | Ile | Ser | Phe | Leu | Asp | Pro | Ala | Ser | |
| 65 | | | | | 70 | | | | | 75 | | | | | 80 | |

| aag | gat | gag | caa | ttg | gcc | ctt | gct | gtt | ctg | gac | aag | ctg | aag | aac | agt | 288 |
| --- | --- | --- | --- | --- | --- | --- | --- | --- | --- | --- | --- | --- | --- | --- | --- | --- |
| Lys | Asp | Glu | Gln | Leu | Ala | Leu | Ala | Val | Leu | Asp | Lys | Leu | Lys | Asn | Ser | |
| | | | | 85 | | | | | 90 | | | | | 95 | | |

| aag | cct | gtg | ttt | ggg | tac | aca | ttc | act | gga | cag | gca | ctt | aac | ttt | att | 336 |
| --- | --- | --- | --- | --- | --- | --- | --- | --- | --- | --- | --- | --- | --- | --- | --- | --- |
| Lys | Pro | Val | Phe | Gly | Tyr | Thr | Phe | Thr | Gly | Gln | Ala | Leu | Asn | Phe | Ile | |
| | | | | 100 | | | | | 105 | | | | | 110 | | |

| tct | gag | gct | gtt | tat | atg | ttt | ggt | gct | agg | cgt | aac | tct | cca | aag | ggc | 384 |
| --- | --- | --- | --- | --- | --- | --- | --- | --- | --- | --- | --- | --- | --- | --- | --- | --- |
| Ser | Glu | Ala | Val | Tyr | Met | Phe | Gly | Ala | Arg | Arg | Asn | Ser | Pro | Lys | Gly | |
| | | 115 | | | | | 120 | | | | | 125 | | | | |

| atc | att | atc | atc | acc | gac | gga | tcc | tct | act | cag | aca | aac | gtt | act | tct | 432 |
| --- | --- | --- | --- | --- | --- | --- | --- | --- | --- | --- | --- | --- | --- | --- | --- | --- |
| Ile | Ile | Ile | Ile | Thr | Asp | Gly | Ser | Ser | Thr | Gln | Thr | Asn | Val | Thr | Ser | |
| 130 | | | | | 135 | | | | | 140 | | | | | | |

| cag | gcg | tcg | gct | cta | cta | agg | gat | gct | ggt | gta | aca | att | cta | gtt | gtt | 480 |
| --- | --- | --- | --- | --- | --- | --- | --- | --- | --- | --- | --- | --- | --- | --- | --- | --- |
| Gln | Ala | Ser | Ala | Leu | Leu | Arg | Asp | Ala | Gly | Val | Thr | Ile | Leu | Val | Val | |
| 145 | | | | 150 | | | | | 155 | | | | | 160 | | |

| gga | gtt | ggg | aag | gct | aaa | gaa | agc | gag | tgt | aga | ggt | ata | gtt | ggt | tgt | 528 |
| --- | --- | --- | --- | --- | --- | --- | --- | --- | --- | --- | --- | --- | --- | --- | --- | --- |
| Gly | Val | Gly | Lys | Ala | Lys | Glu | Ser | Glu | Cys | Arg | Gly | Ile | Val | Gly | Cys | |
| | | | | 165 | | | | | 170 | | | | | 175 | | |

| tct | acc | aaa | gga | gag | tgc | ccc | ctt | ttc | ttt | atg | acc | aac | tgg | gat | gaa | 576 |
| --- | --- | --- | --- | --- | --- | --- | --- | --- | --- | --- | --- | --- | --- | --- | --- | --- |
| Ser | Thr | Lys | Gly | Glu | Cys | Pro | Leu | Phe | Phe | Met | Thr | Asn | Trp | Asp | Glu | |
| | | | 180 | | | | | 185 | | | | | 190 | | | |

| att | atc | agg | aag | gtt | ggg | gag | ttg | atg | gct | gag | gtt | tgt | gag | acc | att | 624 |
| --- | --- | --- | --- | --- | --- | --- | --- | --- | --- | --- | --- | --- | --- | --- | --- | --- |
| Ile | Ile | Arg | Lys | Val | Gly | Glu | Leu | Met | Ala | Glu | Val | Cys | Glu | Thr | Ile | |
| | | 195 | | | | | 200 | | | | | 205 | | | | |

| cct | aag | gac | gcc | gta | tgt | aag | ccg | atc | tgg | tct | gat | tgg | tct | aag | tgt | 672 |
| --- | --- | --- | --- | --- | --- | --- | --- | --- | --- | --- | --- | --- | --- | --- | --- | --- |
| Pro | Lys | Asp | Ala | Val | Cys | Lys | Pro | Ile | Trp | Ser | Asp | Trp | Ser | Lys | Cys | |
| 210 | | | | | 215 | | | | | 220 | | | | | | |

| gac | gcc | aag | tgc | ggc | att | ggg | acg | agg | tac | caa | aag | ttg | atg | gga | gtt | 720 |
| --- | --- | --- | --- | --- | --- | --- | --- | --- | --- | --- | --- | --- | --- | --- | --- | --- |
| Asp | Ala | Lys | Cys | Gly | Ile | Gly | Thr | Arg | Tyr | Gln | Lys | Leu | Met | Gly | Val | |
| 225 | | | | 230 | | | | | 235 | | | | | 240 | | |

```
act aca att tct gag cca act gtc gga acg aac ggc aag tcc ggg agg     768
Thr Thr Ile Ser Glu Pro Thr Val Gly Thr Asn Gly Lys Ser Gly Arg
            245                 250                 255 aca tgt gag atg att tat gag aac gtc gag gtt cca aag gag gag tgc     816
Thr Cys Glu Met Ile Tyr Glu Asn Val Glu Val Pro Lys Glu Glu Cys
        260                 265                 270 tcc gtt gag tct aag att gct gga gga gtg gct cta gca ctg tta atg     864
Ser Val Glu Ser Lys Ile Ala Gly Gly Val Ala Leu Ala Leu Leu Met
    275                 280                 285 ctt gca ggc gga ggt ggt tac aca tac tac aaa aag tac ggt tta tct     912
Leu Ala Gly Gly Gly Gly Tyr Thr Tyr Tyr Lys Lys Tyr Gly Leu Ser
290                 295                 300 aga gtg agt gaa act acg aat ttg gat gag gat ttt gca gat tct agt     960
Arg Val Ser Glu Thr Thr Asn Leu Asp Glu Asp Phe Ala Asp Ser Ser
305                 310                 315                 320 ggg aac cgt ggt gta agg gag agt gtg ggt gaa gct tac aca gta act    1008
Gly Asn Arg Gly Val Arg Glu Ser Val Gly Glu Ala Tyr Thr Val Thr
                325                 330                 335 gat tta gat gat gga ctc tgg agc caa tcc aat caa taa                1047
Asp Leu Asp Asp Gly Leu Trp Ser Gln Ser Asn Gln
                340                 345

<210> SEQ ID NO 8
<211> LENGTH: 348
<212> TYPE: PRT
<213> ORGANISM: Theileria annulata

<400> SEQUENCE: 8

Asp Lys Gly Leu Tyr Pro Asp Gly Ile Lys Lys Pro Ser Ser Tyr Cys
1               5                   10                  15

His Arg Glu Leu Asp Leu Thr Ile Leu Val Asp Glu Ser Ser Ser Ile
            20                  25                  30

Tyr Ile Glu Glu Trp Asn Lys Leu Ile Pro Phe Leu Lys Ser Leu Val
        35                  40                  45

Arg Ser Ile Asn Ile Ser Pro Asn Tyr Val His Leu Ser Met Val Thr
    50                  55                  60

Phe Ser Thr Ser Ile Arg Trp Leu Ile Ser Phe Leu Asp Pro Ala Ser
65                  70                  75                  80

Lys Asp Glu Gln Leu Ala Leu Ala Val Leu Asp Lys Leu Lys Asn Ser
                85                  90                  95

Lys Pro Val Phe Gly Tyr Thr Phe Thr Gly Gln Ala Leu Asn Phe Ile
            100                 105                 110

Ser Glu Ala Val Tyr Met Phe Gly Ala Arg Arg Asn Ser Pro Lys Gly
        115                 120                 125

Ile Ile Ile Ile Thr Asp Gly Ser Ser Thr Gln Thr Asn Val Thr Ser
    130                 135                 140

Gln Ala Ser Ala Leu Leu Arg Asp Ala Gly Val Thr Ile Leu Val Val
145                 150                 155                 160

Gly Val Gly Lys Ala Lys Glu Ser Glu Cys Arg Gly Ile Val Gly Cys
                165                 170                 175

Ser Thr Lys Gly Glu Cys Pro Leu Phe Phe Met Thr Asn Trp Asp Glu
            180                 185                 190

Ile Ile Arg Lys Val Gly Glu Leu Met Ala Glu Val Cys Glu Thr Ile
        195                 200                 205

Pro Lys Asp Ala Val Cys Lys Pro Ile Trp Ser Asp Trp Ser Lys Cys
    210                 215                 220
```

-continued

```
Asp Ala Lys Cys Gly Ile Gly Thr Arg Tyr Gln Lys Leu Met Gly Val
225                 230                 235                 240

Thr Thr Ile Ser Glu Pro Thr Val Gly Thr Asn Gly Lys Ser Gly Arg
            245                 250                 255

Thr Cys Glu Met Ile Tyr Glu Asn Val Glu Val Pro Lys Glu Glu Cys
        260                 265                 270

Ser Val Glu Ser Lys Ile Ala Gly Gly Val Ala Leu Ala Leu Leu Met
    275                 280                 285

Leu Ala Gly Gly Gly Tyr Thr Tyr Tyr Lys Lys Tyr Gly Leu Ser
290                 295                 300

Arg Val Ser Glu Thr Thr Asn Leu Asp Glu Asp Phe Ala Asp Ser Ser
305                 310                 315                 320

Gly Asn Arg Gly Val Arg Glu Ser Val Gly Glu Ala Tyr Thr Val Thr
            325                 330                 335

Asp Leu Asp Asp Gly Leu Trp Ser Gln Ser Asn Gln
            340                 345
```

<210> SEQ ID NO 9
<211> LENGTH: 2259
<212> TYPE: DNA
<213> ORGANISM: Babesia bovis
<220> FEATURE:
<221> NAME/KEY: CDS
<222> LOCATION: (552)..(2

-continued

```
                  80                      85                      90
tta aaa aaa tat gaa gga ata aat gtt tca cta ata agg tac aat agt      878
Leu Lys Lys Tyr Glu Gly Ile Asn Val Ser Leu Ile Arg Tyr Asn Ser
     95                 100                 105 gaa gaa ccg tta ggt tcg acg aaa gca tta acc aac ggg gag ttg aaa      926
Glu Glu Pro Leu Gly Ser Thr Lys Ala Leu Thr Asn Gly Glu Leu Lys
110                 115                 120                 125 aaa cta tcc gat aat att cct act aaa atg cct ttt gac att ggc gtt      974
Lys Leu Ser Asp Asn Ile Pro Thr Lys Met Pro Phe Asp Ile Gly Val
                130                 135                 140 gtt cct act ggt ata gga gct gcc ctc aaa cag ata aaa aca ttg tac     1022
Val Pro Thr Gly Ile Gly Ala Ala Leu Lys Gln Ile Lys Thr Leu Tyr
            145                 150                 155 cct gat cac gaa aag ttc ctt gtt ggg aac acc att act gag ttg gat     1070
Pro Asp His Glu Lys Phe Leu Val Gly Asn Thr Ile Thr Glu Leu Asp
        160                 165                 170 tat tct aaa gca ttg ggt aag gat att gtt gta atc gtg ttt act act     1118
Tyr Ser Lys Ala Leu Gly Lys Asp Ile Val Val Ile Val Phe Thr Thr
    175                 180                 185 ggc cac gtc att gat cca tat tta gca tat gat gag gca ttt gat gcc     1166
Gly His Val Ile Asp Pro Tyr Leu Ala Tyr Asp Glu Ala Phe Asp Ala
190                 195                 200                 205 cgc cgt aat ggt gta aga ttt tac gtt att aat agg gga gga aag gca     1214
Arg Arg Asn Gly Val Arg Phe Tyr Val Ile Asn Arg Gly Gly Lys Ala
                210                 215                 220 aaa aac tat tgg act cag cta ttg gga tgc cac tac aat act tgt ttg     1262
Lys Asn Tyr Trp Thr Gln Leu Leu Gly Cys His Tyr Asn Thr Cys Leu
            225                 230                 235 agt tat att cgg gcc aaa ata aca agg cct tca cta tat ctc gat gtt     1310
Ser Tyr Ile Arg Ala Lys Ile Thr Arg Pro Ser Leu Tyr Leu Asp Val
        240                 245                 250 ttg gtg aac agg att gtg tct aaa cgc gcg aaa gat gcc gtt tgt ttg     1358
Leu Val Asn Arg Ile Val Ser Lys Arg Ala Lys Asp Ala Val Cys Leu
    255                 260                 265 gaa gtg tgg acg gat tat aaa cct aac act gaa aaa tcg gat gtg agg     1406
Glu Val Trp Thr Asp Tyr Lys Pro Asn Thr Glu Lys Ser Asp Val Arg
270                 275                 280                 285 att atg act tct acg ttg aaa tta tac aaa acc ctt ctt act gga agc     1454
Ile Met Thr Ser Thr Leu Lys Leu Tyr Lys Thr Leu Leu Thr Gly Ser
                290                 295                 300 ttt gcg gag ara aac atc aaa ggt ctc aca tgt gat gag cag cta aag     1502
Phe Ala Glu Xaa Asn Ile Lys Gly Leu Thr Cys Asp Glu Gln Leu Lys
            305                 310                 315 gat atg cag aaa aga caa ata ttt tgc tac tca aat aag tgt gct ccc     1550
Asp Met Gln Lys Arg Gln Ile Phe Cys Tyr Ser Asn Lys Cys Ala Pro
        320                 325                 330 acg atc tat tca aga tct tat gtt gac tta gct att caa cgt ctt aat     1598
Thr Ile Tyr Ser Arg Ser Tyr Val Asp Leu Ala Ile Gln Arg Leu Asn
    335                 340                 345 gca aaa gat ttt aaa gag gta cta gat gag tca tct tac aga tca cgc     1646
Ala Lys Asp Phe Lys Glu Val Leu Asp Glu Ser Ser Tyr Arg Ser Arg
350                 355                 360                 365 agt ttg caa tca gtg gag aaa cat aat gag caa caa aca ggt tct caa     1694
Ser Leu Gln Ser Val Glu Lys His Asn Glu Gln Gln Thr Gly Ser Gln
                370                 375                 380 gaa acg ctt tct gga agc gcc cgt gta gaa aca agc tta gaa agc tca     1742
Glu Thr Leu Ser Gly Ser Ala Arg Val Glu Thr Ser Leu Glu Ser Ser
            385                 390                 395 gta cct tca tcc tat gtg gca gaa ttg gga gaa agt gat aca gaa aca     1790
```

```
tac aaa cag ttg gag tac ata gat aaa aat ggc gtc act gtc ttc aac     1838
Tyr Lys Gln Leu Glu Tyr Ile Asp Lys Asn Gly Val Thr Val Phe Asn
    415                 420                 425 gat gag ccc act gtt gtt gtc gat act ccc gag tac gta caa aag gtg     1886
Asp Glu Pro Thr Val Val Val Asp Thr Pro Glu Tyr Val Gln Lys Val
430                 435                 440                 445 cat gaa aga gaa atg cag ttt gat gaa gaa tcc acc cat ctt ccc aac     1934
His Glu Arg Glu Met Gln Phe Asp Glu Glu Ser Thr His Leu Pro Asn
                450                 455                 460 tct ggt aac cac cat cca cct cat cac cga aag ggg gcc aac gga tcc     1982
Ser Gly Asn His His Pro Pro His His Arg Lys Gly Ala Asn Gly Ser
            465                 470                 475 ggt aaa aag acc acg atc gtc gtt ggt att ata tgc ctt gta gta ata     2030
Gly Lys Lys Thr Thr Ile Val Val Gly Ile Ile Cys Leu Val Val Ile
        480                 485                 490 tgc gcc gtc ata gcc ggc gcc tac cta tcc ctt tca cag caa gag tct     2078
Cys Ala Val Ile Ala Gly Ala Tyr Leu Ser Leu Ser Gln Gln Glu Ser
    495                 500                 505 gtg gaa ctc acc tct gaa gag ggt gac ttc ttg aac gac act acg ggt     2126
Val Glu Leu Thr Ser Glu Glu Gly Asp Phe Leu Asn Asp Thr Thr Gly
510                 515                 520                 525 ggt caa cct gag gta ctc gaa aca caa cag gtt gtg gat gca gag aac     2174
Gly Gln Pro Glu Val Leu Glu Thr Gln Gln Val Val Asp Ala Glu Asn
                530                 535                 540 aaa aca tgg ttg taa gacacgaaac gggttgtcac agccaacata tacaaatgca    2229
Lys Thr Trp Leu
            545 gtttaaatta agtcactagt taaaaaaaaa                                    2259

<210> SEQ ID NO 10
<211> LENGTH: 545
<212> TYPE: PRT
<213> ORGANISM: Babesia bovis
<220> FEATURE:
<221> NAME/KEY: misc_feature
<222> LOCATION: (305)..(305)
<223> OTHER INFORMATION: The 'Xaa' at location 305 stands for
      Arg, or Lys.

<400> SEQUENCE: 10

Met Val Lys Phe His Thr Leu Ser Val Ala Ala Ile Leu Ala Ile Ala
1               5                   10                  15

Ser Ser Asn Thr Ile Phe Ala Thr Phe Arg Ser Asn Gly Lys Thr Phe
            20                  25                  30

Gly Asp Glu Ser Val Ser Leu Leu Glu His Glu Ser Thr Ser Leu Ser
        35                  40                  45

Arg Gly Pro Arg Pro Thr Glu Asp Gln Ile Ser Gln Leu Pro Lys Asn
    50                  55                  60

Val Phe Phe Leu Leu Asp Asn Ser Ile Asp Met Ser Ile Glu Thr Gly
65                  70                  75                  80

Glu Glu Asn Arg His Phe Leu Ser Glu Phe Phe Lys Leu Leu Lys Lys
                85                  90                  95

Tyr Glu Gly Ile Asn Val Ser Leu Ile Arg Tyr Asn Ser Glu Glu Pro
            100                 105                 110

Leu Gly Ser Thr Lys Ala Leu Thr Asn Gly Glu Leu Lys Lys Leu Ser
        115                 120                 125

Asp Asn Ile Pro Thr Lys Met Pro Phe Asp Ile Gly Val Val Pro Thr
```

```
                130                 135                 140
Gly Ile Gly Ala Ala Leu Lys Gln Ile Lys Thr Leu Tyr Pro Asp His
145                 150                 155                 160

Glu Lys Phe Leu Val Gly Asn Thr Ile Thr Glu Leu Asp Tyr Ser Lys
                165                 170                 175

Ala Leu Gly Lys Asp Ile Val Ile Val Phe Thr Thr Gly His Val
                180                 185                 190

Ile Asp Pro Tyr Leu Ala Tyr Asp Glu Ala Phe Asp Ala Arg Arg Asn
                195                 200                 205

Gly Val Arg Phe Tyr Val Ile Asn Arg Gly Lys Ala Lys Asn Tyr
    210                 215                 220

Trp Thr Gln Leu Leu Gly Cys His Tyr Asn Thr Cys Leu Ser Tyr Ile
225                 230                 235                 240

Arg Ala Lys Ile Thr Arg Pro Ser Leu Tyr Leu Asp Val Leu Val Asn
                245                 250                 255

Arg Ile Val Ser Lys Arg Ala Lys Asp Ala Val Cys Leu Glu Val Trp
                260                 265                 270

Thr Asp Tyr Lys Pro Asn Thr Glu Lys Ser Asp Val Arg Ile Met Thr
                275                 280                 285

Ser Thr Leu Lys Leu Tyr Lys Thr Leu Leu Thr Gly Ser Phe Ala Glu
    290                 295                 300

Xaa Asn Ile Lys Gly Leu Thr Cys Asp Glu Gln Leu Lys Asp Met Gln
305                 310                 315                 320

Lys Arg Gln Ile Phe Cys Tyr Ser Asn Lys Cys Ala Pro Thr Ile Tyr
                325                 330                 335

Ser Arg Ser Tyr Val Asp Leu Ala Ile Gln Arg Leu Asn Ala Lys Asp
                340                 345                 350

Phe Lys Glu Val Leu Asp Glu Ser Ser Tyr Arg Ser Arg Ser Leu Gln
                355                 360                 365

Ser Val Glu Lys His Asn Glu Gln Gln Thr Gly Ser Gln Glu Thr Leu
    370                 375                 380

Ser Gly Ser Ala Arg Val Glu Thr Ser Leu Glu Ser Ser Val Pro Ser
385                 390                 395                 400

Ser Tyr Val Ala Glu Leu Gly Glu Ser Asp Thr Glu Thr Tyr Lys Gln
                405                 410                 415

Leu Glu Tyr Ile Asp Lys Asn Gly Val Thr Val Phe Asn Asp Glu Pro
                420                 425                 430

Thr Val Val Asp Thr Pro Glu Tyr Val Gln Lys Val His Glu Arg
                435                 440                 445

Glu Met Gln Phe Asp Glu Glu Ser Thr His Leu Pro Asn Ser Gly Asn
450                 455                 460

His His Pro Pro His His Arg Lys Gly Ala Asn Gly Ser Gly Lys Lys
465                 470                 475                 480

Thr Thr Ile Val Val Gly Ile Ile Cys Leu Val Val Ile Cys Ala Val
                485                 490                 495

Ile Ala Gly Ala Tyr Leu Ser Leu Ser Gln Gln Glu Ser Val Glu Leu
                500                 505                 510

Thr Ser Glu Glu Gly Asp Phe Leu Asn Asp Thr Thr Gly Gly Gln Pro
                515                 520                 525

Glu Val Leu Glu Thr Gln Gln Val Asp Ala Glu Asn Lys Thr Trp
    530                 535                 540

Leu
545
```

<210> SEQ ID NO 11
<211> LENGTH: 22
<212> TYPE: DNA
<213> ORGANISM: Artificial
<220> FEATURE:
<223> OTHER INFORMATION: primer 1

<400> SEQUENCE: 11
ccacggctct ggaatctatg tc                                            22

<210> SEQ ID NO 12
<211> LENGTH: 24
<212> TYPE: DNA
<213> ORGANISM: Artificial
<220> FEATURE:
<223> OTHER INFORMATION: primer 2

<400> SEQUENCE: 12
caaaaggata cctatatttg gtac                                          24

<210> SEQ ID NO 13
<211> LENGTH: 27
<212> TYPE: DNA
<213> ORGANISM: Artificial
<220> FEATURE:
<223> OTHER INFORMATION: Primer 3

<400> SEQUENCE: 13
tgtggtagat gaatctgcta gtatatc                                       27

<210> SEQ ID NO 14
<211> LENGTH: 27
<212> TYPE: DNA
<213> ORGANISM: Artificial
<220> FEATURE:
<223> OTHER INFORMATION: Primer 4

<400> SEQUENCE: 14
ctatgccacg gcattcagca acattta                                       27

<210> SEQ ID NO 15
<211> LENGTH: 27
<212> TYPE: DNA
<213> ORGANISM: Artificial
<220> FEATURE:
<223> OTHER INFORMATION: Primer 5

<400> SEQUENCE: 15
cccggatcca tgcagttaca taacaaa                                       27

<210> SEQ ID NO 16
<211> LENGTH: 27
<212> TYPE: DNA
<213> ORGANISM: Artificial
<220> FEATURE:
<223> OTHER INFORMATION: Primer 6

<400> SEQUENCE: 16
gggaagcttc tgagcaaagg aaatagg                                       27

<210> SEQ ID NO 17
<211> LENGTH: 27
<212> TYPE: DNA
<213> ORGANISM: Artificial
<220> FEATURE:

-continued

```
<223> OTHER INFORMATION: Primer 7

<400> SEQUENCE: 17
cccgaattcg tggtagatga atctgct                                              27

<210> SEQ ID NO 18
<211> LENGTH: 29
<212> TYPE: DNA
<213> ORGANISM: Artificial
<220> FEATURE:
<223> OTHER INFORMATION: Primer 8

<400> SEQUENCE: 18
cccgtcgact gcctcgcccc aaatgttgt                                            29

<210> SEQ ID NO 19
<211> LENGTH: 30
<212> TYPE: DNA
<213> ORGANISM: Artificial
<220> FEATURE:
<223> OTHER INFORMATION: Primer 9

<400> SEQUENCE: 19
cccgaattcc atgatggtga agttccacac                                           30

<210> SEQ ID NO 20
<211> LENGTH: 29
<212> TYPE: DNA
<213> ORGANISM: Artificial
<220> FEATURE:
<223> OTHER INFORMATION: Primer 10

<400> SEQUENCE: 20
cccgtcgacg ttggccccct ttcggtgat                                            29
```